US008389561B2

(12) United States Patent
Stevens et al.

(10) Patent No.: US 8,389,561 B2
(45) Date of Patent: Mar. 5, 2013

(54) SUBSTITUTED 7-AZABICYCLO[2.2.1]HEPTYL DERIVATIVES USEFUL FOR MAKING PHARMACEUTICAL COMPOSITIONS

(75) Inventors: Christian Stevens, Merelbeke (BE); Ann De Blieck, Ninove (BE); Thomas Heugebaert, Marke (BE)

(73) Assignee: Universiteit Gent, Ghent (BE)

( * ) Notice: Subject to any disclaimer, the term of this patent is extended or adjusted under 35 U.S.C. 154(b) by 527 days.

(21) Appl. No.: 12/612,452

(22) Filed: Nov. 4, 2009

(65) Prior Publication Data

US 2010/0093807 A1    Apr. 15, 2010

Related U.S. Application Data

(63) Continuation-in-part of application No. 12/188,524, filed on Aug. 8, 2008, now Pat. No. 7,884,125.

(60) Provisional application No. 61/049,023, filed on Apr. 30, 2008.

(51) Int. Cl.
*A61K 31/403* (2006.01)
*C07D 221/22* (2006.01)
(52) U.S. Cl. ............ 514/413; 548/452; 548/465
(58) Field of Classification Search .......... 514/413; 548/452, 465
See application file for complete search history.

(56) References Cited

U.S. PATENT DOCUMENTS

| | | | |
|---|---|---|---|
| 5,510,490 | A | 4/1996 | Pandey et al. |
| 5,817,679 | A | 10/1998 | Shen et al. |
| 6,060,473 | A | 5/2000 | Shen et al. |
| 6,077,846 | A | 6/2000 | Qian et al. |
| 6,117,889 | A | 9/2000 | Shen et al. |
| 6,562,816 | B2 | 5/2003 | Wishka et al. |
| 2009/0275616 | A1 | 11/2009 | Stevens et al. |
| 2010/0093807 | A1 | 4/2010 | Stevens et al. |

FOREIGN PATENT DOCUMENTS

| | | |
|---|---|---|
| CA | 2 638 573 | 10/2009 |
| EP | 0 657 455 | 6/1995 |
| EP | 0 955 301 | 11/1999 |
| WO | WO 90/07503 | 7/1990 |
| WO | WO 00/23424 | 4/2000 |
| WO | WO 2007/137030 | 11/2007 |
| WO | WO-2007/137030 A2 * | 11/2007 |

OTHER PUBLICATIONS

Office Communication to Canadian Patent Application No. 2,638,573, dated Jan. 20, 2012 (2 pages).
Office Action for U.S. Appl. No. 12/188,524, dated Mar. 29, 2010.
Radchenko et al., "Conformationally Restricted Nonchiral Pipecolic Acid Analogues," *J. Org. Chem.* 74(15):5541-5544 (2009).
Search Report for British Patent Application No. GB 0919325.1, dated Mar. 1, 2010.
Dunlop et al., "In Vitro Screening Strategies for Nicotinic Receptor Ligands" *Biochemical Pharmacology* 74:1172-1181 (2007).
Grygorenko et al., "Stereoselective Synthesis of 2,4-methanoproline Homologues" *Tetrahedron: Asymmetry* 17:252-258 (2006).
Cheng et al., "Synthesis and Biological Evaluation at Nicotinic Acetylcholine Receptors of N-Arylalkyl- and N-Aryl-7-Azabicyclo[2.2.1]heptanes," *J. Med Chem.* 45: 3041-3047 (2002).
Krow et al., "Synthesis of 5- and 6-(6-Chloro-3-pyridyl)-2-azabicyclo[2.2.0]hexanes. Epibatidine Analogs," *Tetrahedron* 56: 9233-9239 (2000).
Xu et al., "Conformationally Constrained Nicotines. 1-Pyridinyl-7-azabicyclo[2.2.1]heptane and 1-Pyridinyl-8-azabicyclo[3.2.1]octane Analogues," *J. Org. Chem.* 64: 4069-4078 (1999).
International Search Report for International Application No. PCT/EP2010/066764, dated Feb. 28, 2011 (dated of completion of search) and Apr. 8, 2011 (date of mailing of report).
Written Opinion of the International Search Authority for International Application No. PCT/EP2010/066764, dated Apr. 8, 2011.
Heugebaert et al., "A Straightforward Entry to 7-Azabicyclo[2,2,1]heptane-1-carbonitriles in the Synthesis of Novel Epibatidine Analogues," *Eur. J. Chem.* 2010:1017-1020, 2010.

* cited by examiner

*Primary Examiner* — Kamal Saeed
*Assistant Examiner* — Janet L Coppins
(74) *Attorney, Agent, or Firm* — Clark & Elbing LLP

(57) ABSTRACT

This invention provides 1-substituted-7-azabicyclo[2.2.1] heptyl derivatives, intermediates and methods for producing them, which are therapeutic agents useful for the prevention and treatment of central nervous system disorders and diseases mediated by a Nicotinic Acetylcholine Receptor such as Alzheimer's disease, Parkinson's disease, schizophrenia, epilepsy, pain, nicotine addiction and dementia.

27 Claims, No Drawings

SUBSTITUTED 7-AZABICYCLO[2.2.1]HEPTYL DERIVATIVES USEFUL FOR MAKING PHARMACEUTICAL COMPOSITIONS

CROSS REFERENCE TO RELATED APPLICATIONS

This application is a continuation-in-part of U.S. patent application Ser. No. 12/188,524 filed Aug. 8, 2008, which claims the benefit of U.S. Provisional Patent Application No. 61/049,023 filed Apr. 30, 2008, the disclosures of which are incorporated by reference in their entirety.

FIELD OF THE INVENTION

The present invention relates to a group of substituted-7-azabicyclo-[2.2.1]heptyl derivatives with biological activity. The present invention also relates to synthetic methods for producing substituted-7-azabicyclo-[2.2.1]heptyl derivatives belonging to this group. The present invention also relates to certain intermediates for producing such substituted-7-azabicyclo-[2.2.1]heptyl derivatives, as well as a synthetic method for producing such intermediates. The present invention also relates to the nicotinic acetylcholine receptor modulating activity of these derivatives and, as a consequence, to pharmaceutical compositions comprising a therapeutically effective amount of such substituted-7-azabicyclo-[2.2.1]heptyl derivatives, as well as their use as medicaments for the prevention and treatment of central nervous system disorders and diseases mediated by a Nicotinic Acetylcholine Receptor, such as pain, Alzheimer's disease, Parkinson's disease, schizophrenia, epilepsy and nicotine addiction.

BACKGROUND OF THE INVENTION

The alkaloid epibatidine, i.e. 2-(6-chloro-3-pyridinyl)-7-azabicyclo[2.2.1]heptane, was first isolated in 1974 from the skin of the Ecuadorian frog *Epipedobates tricolor*. Shortly afterwards, its analgesic potency was shown to be about 200-fold higher than that of morphine. Regrettably however, the toxicity of epibatidine is too high for any human therapeutic use. The mode of action of epibatidine was later revealed as a highly potent nicotinic acetylcholine receptor agonist. The membrane bound pentameric ion channel has been associated with many neurological disorders such as Alzheimer's disease, Parkinson disease and schizophrenia. For each of these disorders, there is a shift in the prevalence of the different nicotinic acetylcholine receptor subtypes.

In order to improve the ratio of pharmacological to toxicological activity, many analogues have been synthesized. Most of them are substituted at position 2 of the 7-azabicyclo-[2.2.1]heptyl ring, e.g. WO 00/23424, U.S. Pat. Nos. 6,060,473, 5,817,679, 6,117,889, 6,077,846, 5,510,490, EP 657,455, U.S. Pat. No. 6,562,816, and EP 955,301. Grygorenko et al in *Tetrahedron* (2006) 17:252 has also disclosed one derivative substituted at position 1 of the 7-azabicyclo-[2.2.1] heptyl ring, i.e. 7-(1-phenylethyl)-7-azabicyclo-[2.2.1]heptyl-1-carbonitrile.

As disclosed by Collingridge et al in *Neuropharmacology* (2009) 56:2-5 (especially table 1) and in accordance with the International Union of Pharmacology Committee on Receptor Nomenclature and Drug Classification, nicotinic acetylcholine receptors (hereinafter nAChR) belong to the Cys-loop superfamily of receptors (also including GABA, 5-HT$_3$, glycine and zinc activated receptors) which itself is part of ligand-gated ion channels activated by neurotransmitters (also named the neurotransmitter-gated ion channel superfamily).

nAChR are widely distributed throughout the central (CNS) and peripheral (PNS) nervous systems. Such receptors play an important role in regulating CNS function, particularly by modulating release of a wide range of neurotransmitters such as acetylcholine, norepinephrine, dopamine, serotonin and GABA, and are consequently involved in a wide variety of complex brain functions such as neurodegeneration, pain and inflammation, psychosis, mood and emotion, memory, attention and cognition as well as in pathological conditions such as Alzheimer's and Parkinson's disease, schizophrenia, epilepsy, pain and nicotine addiction. At least 16 different genes code for nAChR subunits, which can assemble as pentamers in different combinations to form diverse nAChR subtypes. nAChR are ligand-gated ion channels formed by the assembly of five subunits (pentamers). Each subunit is comprised of a large extracellular N-terminal. The agonist binding site is located in the N-terminal, at the interface between two adjacent subunits. 17 distinct nAChR subunits have been identified. Besides the muscular nAChR subtypes, the neuronal nAChR can be divided in two groups:

α-bungarotoxin sensitive receptors which can be homomeric (being composed of five α7 or α9 subunits) or heteromeric (made up of different α7 or α9 or α10 subunits); and α-bungarotoxin insensitive receptors which consist of different heteromeric combinations of α(α2-α6) and β (β2-β4) subunits, whose prevalent stoichiometry is believed to be $(\alpha)_2(\beta)_3$.

The α7 subtype and the predominant α4β2 subtypes of nAChR have been recognized as being of major importance since they play a significant role in enhancing cognitive function, protection against neuron degeneration, schizophrenia and pain relief. The activity of both α7 and α4β2 nAChR can be modified or regulated by means of subtype-selective nAChR ligands which can exhibit antagonist, agonist or partial agonist properties. The number of binding sites depends on the number and type of α subunits: for instance in $(\alpha7)_5$, five identical binding sites are present, whereas in $(\alpha4)_2(\beta2)_3$ there are two binding sites located at the interface between the α4 and β2 subunits.

α7 subunits uniquely and efficiently assemble into functional homopentameric acetylcholine-gated non selective cation channels when expressed in mammalian cells. The α4β2 and α3β4 subtypes are also well characterized in terms of ligand selectivity. A few other subtypes such as α2β4, α4β4, α3β2, and α1β1γδ, have also been evaluated for instance by Broad et al in *J. Pharmacol. Exper. Therap.* (2006) 318:1108-1117. There is currently significant interest in developing selective nAChR agonists and modulators, in particular selective ligands for the α7, α4β2, α3β4 α2β4, α4β4, α3β2, and α1β1γδ subtypes of nAChR, for the treatment of various neurological, neurodegenerative and psychiatric disorders.

More particular, there is still a need in the art for more subtype selective nAChR modulators such as epibatidine analogues in an effort to provide prevention or treatment for neurological, neurodegenerative and psychiatric diseases such as, but not limited to, Alzheimer disease, Parkinson disease, epilepsy, pain, nicotine addiction, mood instability, dementia and schizophrenia, as well as other CNS disorders such as impaired memory performance, impaired attention and cognitive deficit. The present invention intends to address one or more of these problems.

SUMMARY OF THE INVENTION

According to a first aspect, the present invention relates to a group of 1-substituted-7-azabicyclo[2.2.1]heptyl derivatives represented by the structural formula (I):

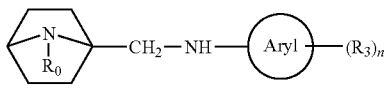

or the structural formula (II):

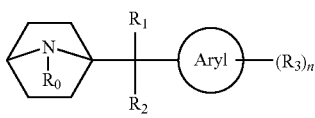

or the structural formula (III):

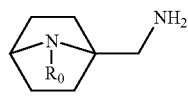

wherein:
R$_0$ is hydrogen or a nitrogen-protecting group selected from the group consisting of benzyl, heteroarylmethyl, heteroarylethyl, phenylethyl, naphthylmethyl, naphthylethyl, butoxycarbonyl, C$_{3-4}$ alkenyl and C$_{1-8}$ alkyl, wherein said benzyl is optionally substituted with one to three substituents independently selected from the group consisting of halogen, C$_{1-4}$ alkyl, C$_{1-4}$ alkoxy, trifluoromethyl, trifluoromethoxy, dimethylaminoethoxy, dimethylamino-propoxy, morpholinoethoxy, phenoxy, phenoxymethyl, heteroaryl and heteroarylmethyl;
R$_1$ is hydrogen and R$_2$ is hydroxyl, or R$_1$ in combination with R$_2$ is oxo or imino;
each R$_3$ is a substituent selected from the group consisting of fluoro, chloro, bromo, C$_{1-4}$ alkyl, C$_{1-4}$ alkoxy, C$_{1-4}$ alkylthio, cyano, phenyl, trifluoromethyl, trifluoromethoxy, amino, dimethylamino, heteroaryl and tert-butylcarboxylate; and
n is 0, 1, 2 or 3; and
Aryl is an optionally substituted aryl or heteroaryl group, or a pharmaceutically acceptable salt thereof, or an enantiomer, or a stereoisomeric form thereof, or a solvate thereof.

Within this broad concept, it can be understood that when at least one substituent R$_3$ of Aryl is a hydrocarbyl group (e.g. alkyl or phenyl), Aryl can be regarded as an arylene or heteroarylene divalent group.

According to a second aspect, the present invention relates to a method for producing 1-substituted-7-azabicyclo[2.2.1] heptyl derivatives represented by the structural formula (I) or the structural formula (III), a method for producing 1-substituted-7-azabicyclo[2.2.1]heptyl derivatives represented by the structural formula (II) wherein R$_1$ is hydrogen and R$_2$ is hydroxyl, and a method for producing 1-substituted-7-azabicyclo[2.2.1]heptyl derivatives represented by the structural formula (II) wherein R$_1$ in combination with R$_2$ is oxo or imino.

According to a third aspect, the present invention relates to a group of 1-formyl-7-R$_0$-substituted-7-azabicyclo[2.2.1]-heptanes and 1-cyano-7-R$_0$-substituted-7-azabicyclo[2.2.1]-heptanes, wherein R$_0$ is hydrogen or a nitrogen-protecting group selected from the group consisting of benzyl, heteroarylmethyl, heteroarylethyl, phenylethyl, naphthylmethyl, naphthylethyl, butoxycarbonyl, C$_{3-4}$ alkenyl and C$_{1-8}$ alkyl, wherein said benzyl is optionally substituted with one to three substituents independently selected from the group consisting of halogen, C$_{1-8}$ alkyl, C$_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl, a method for producing them, and their use as intermediates for producing the 1-substituted-7-azabicyclo[2.2.1]heptyl derivatives represented by the above structural formulae (I), (II) and (III).

According to a fourth aspect, the present invention relates to pharmaceutical compositions comprising a therapeutically effective amount of a 1-substituted-7-azabicyclo[2.2.1]-heptyl derivative represented by the structural formula (I) or the structural formula (II) or the structural formula (III). These pharmaceutical compositions are useful as medicaments for the prevention or treatment of diseases or disorders mediated by a Nicotinic Acetylcholine Receptor or another receptor belonging to the Cys-loop superfamily of receptors. Such diseases or disorders include, but are not limited to, pain, Alzheimer's disease, Parkinson's disease, schizophrenia, epilepsy, dementia and nicotine addiction. These pharmaceutical compositions are also useful for the prevention or treatment of other CNS disorders such as impaired memory performance, impaired attention and cognitive deficit.

DEFINITIONS

As used herein with respect to a substituting group, and unless otherwise stated, the term "C$_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl (isobutyl) and 1,1-dimethylethyl (ter-butyl). By analogy, the term "C$_{1-8}$ alkyl" refers to such groups having from 1 to 8 carbon atoms, including 2-methylbutyl, n-pentyl, dimethylpropyl, n-hexyl, 2-methylpentyl, 3-methylpentyl, n-heptyl, n-octyl, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-C$_{4-8}$ cycloalkyl groups such as, for instance, indanyl, tetrahydronaphthyl, fluorenyl and the like, all of the said groups being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the term "C$_{1-4}$ alkoxy" refers to substituents wherein a carbon atom of a C$_{1-4}$ alkyl group (such as defined herein), is attached to an oxygen atom through a single bond such as, but not limited to, methoxy, ethoxy, propoxy, n-butoxy, pentoxy, isopropoxy, sec-butoxy, and tert-butoxy.

As used herein and unless otherwise stated, the term "stereoisomeric form" refers to all possible different isomeric as well as conformational forms which the compounds of this invention may exhibit, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or a suitable organic solvent such as, but not limited to, alcohols (thus forming alcoholates), ketones, esters, ethers, nitriles (e.g. acetonitrile) and the like.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

As used herein, the term "schizophrenia" refers to a complex psychosis characterised by abnormalities in perception, content of thought, and thought processes (hallucinations) and by extensive withdrawal of interest from the outside world and excessive focusing on one's own mental life.

As used herein, the term "dementia" refers to a pathologic condition characterised by disorientation, impaired memory and judgment, and the usually progressive loss of cognitive and intellectual functions without impairment of perception or consciousness. The term encompasses various specific forms such as, but not limited to, epileptic dementia, hebephrenic dementia, Lewy body dementia, presenile dementia and the like.

As used herein, the term "pain" refers to an unpleasant abnormal sensory or emotional experience subjectively described as a potential tissue damage, usually in response or due to a stimulus which does not normally provoke such experience. It includes pain initiated or caused by a lesion or dysfunction in the central nervous system, and other specific forms such as detailed in the 2007 edition of the pain terminology published by the International Association for the Study of Pain. This definition refers to use in clinical practice rather than for experimental work, physiology or anatomical purpose.

As used herein with respect to a substituting group, and unless otherwise stated, the term "heteroaryl" refers to a mono- or polycyclic, aromatically unsaturated monovalent hydrocarbon group having from 2 up to 15 carbon atoms and including one or more heteroatoms in one or more rings, each of said rings having from 3 to 10 atoms (and optionally further including one or more heteroatoms attached to one or more carbon atoms of said ring, for instance in the form of a carbonyl or thiocarbonyl or selenocarbonyl group, each of said heteroatoms being independently selected from the group consisting of nitrogen, oxygen and sulfur, also including groups wherein a heterocyclic ring is fused to one or more aromatic hydrocarbon rings for instance in the form of benzo-fused, dibenzo-fused or naphtho-fused heterocyclic groups, and also including groups wherein each carbon atom of each ring may furthermore be independently substituted with a substituent selected from the group consisting of halogen, nitro, $C_{1-4}$ alkyl (optionally containing, in the main chain or a side chain, one or more atoms or groups such as oxo, hydroxyl, ether, thioether, acetal, amino, or halogen). Within the framework of the present invention, heteroaryl groups including one or more nitrogen atoms in one or more rings are highly preferred. Within the broad definition hereinabove are included heterocyclic aromatically unsaturated groups such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxazepinyl, benzothiazepinyl, benzodiazepinyl, benzoxazocinyl, benzothiazocinyl, benzodiazocinyl, benzoxathiocinyl, benzoxathiazepinyl, benzoxadiazepinyl, benzothiadiazepinyl, benzotriazepinyl, benzotriazinonyl, benzoxazolinonyl, azetidinonyl, azaspiroundecyl, selenazinyl, selenazolyl, selenophenyl, azahypoxanthinyl, bipyrazinyl, bipyridinyl, oxazolidinyl, diselenopyrimidinyl, benzophenazinyl, benzoquinolizinyl, dibenzocarbazolyl, dibenzoacridinyl, dibenzophenazinyl, dibenzoquinoxalinyl, dibenzothiazepinyl, dibenzisoquinolinyl, tetraazaadamantyl, thiatetraazaadamantyl, oxauracil, oxazinyl, oxazolinyl, oxazolonyl, azaindolyl, azolonyl, thiazolinyl, thiazolonyl, thiazolidinyl, thiazanyl, pyrimidonyl, thiopyrimidonyl, azlactonyl, naphthindazolyl, naphthindolyl, naphthothiazolyl, naphthothioxolyl, naphthoxindolyl, naphthotriazolyl, azabenzimidazolyl, azacycloheptyl, azacyclooctyl, azacyclononyl, azabicyclononyl, dioxindolyl, dioxazinyl, thiourazolyl, thiotriazolyl, quinoleinyl, oxyquinoleinyl, quinuclidinyl, xanthinyl, dihydropyranyl, benzodihydrofuryl, benzothiopyronyl, benzothiopyronyl, benzoxazinyl, benzoxazolyl, benzodioxolyl, benzodioxanyl, benzothiadiazolyl, benzotriazinyl, benzothiazolyl, benzoxazolyl, phenothiazolyl, phenoxazolyl, pyridinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, hydantoinyl, indolyl, indazolyl, quinolyl, quinazolinyl, quinoxalinyl, carbazolyl, phenoxazinyl, phenothiazinyl, xanthenyl, purinyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, benzimidazolyl, uridinyl, thymidinyl, cytidinyl, azirinyl, aziridinyl, diazirinyl, diaziridinyl, oxaziridinyl, azetyl, azetidinyl, diazabicyclooctyl, diazetyl, diaziridinonyl, diaziridinethionyl, benzisothiazolyl, benzocarbazolyl, benzisoalloxazinyl, phenometoxazinyl, phenoparoxazinyl, phentriazinyl, thiodiazinyl, thiodiazolyl, benzodiazinyl (e.g. phtalazinyl), phthalidyl, phthalimidinyl, phtalazonyl, alloxazinyl, isatyl, isopyrazolyl, isopyrazolonyl, urazolyl, urazinyl, uretinyl, uretidinyl, and the like, including all possible isomeric forms thereof. Within the above list, heteroaryl groups including one or more nitrogen atoms in one or more rings are highly preferred.

As used herein with respect to a substituting group, and unless otherwise stated, the term "arylene" designate a divalent hydrocarbon group derived from "aryl" by abstracting a hydrogen atom.

As used herein with respect to a substituting group, and unless otherwise stated, the term "heteroarylene" designate a divalent hydrocarbon group derived from "heteroaryl" by abstracting a hydrogen atom.

DETAILED DESCRIPTION OF THE INVENTION

The present invention relates to various groups of novel 1-substituted-7-azabicyclo[2.2.1]heptyl derivatives which have desirable biological properties such as, but not limited to, modulating the activity of a Nicotinic Acetylcholine Receptor (nAChR) e.g. by binding, preferably selectively is binding, to one or more subunits of a nAChR subtype, or modulating the activity of another receptor belonging to the Cys-loop superfamily of receptors.

Preferably a 1-substituted-7-azabicyclo[2.2.1]heptyl derivative represented by the structural formula (I) or the structural formula (II) or the structural formula (III) is able to modulate, preferably selectively modulate, the activity of one or more of the α7 subtype, the α4β2 subtype, the α3β4 subtype, the α2β4 subtype, the α4β4 subtype, the α3β2 subtype, and the α1β1γδ subtype, of nAChR. Based on this biological activity, and the fact that these compounds are not toxic to human cells, these compounds are useful in the prevention and/or treatment of a disease mediated by a Nicotinic Acetylcholine Receptor such as, but not limited to, pain, Alzheimer's disease, Parkinson's disease, schizophrenia, epilepsy, dementia and nicotine addiction, or for the prevention or treatment of other central nervous system disorders such as impaired memory performance, impaired attention and cognitive deficit. They may also be useful in the prevention and/or treatment of a disease mediated by another receptor belonging to the Cys-loop superfamily of receptors.

In the broadest expression, the class of novel biologically active 1-substituted-7-azabicyclo[2.2.1]heptyl derivatives according to the first aspect of this invention may be represented by the structural formula (I) or the structural formula (II) or the structural formula (III), including stereoisomers, solvates and pharmaceutically acceptable salts thereof. This broad class may be sub-divided into several sub-classes wherein each substituent $R_0$ to $R_3$, and/or the Aryl group may independently be defined in a more restricted manner, at will and independently from each other. Exemplary but non-limiting embodiments of such sub-classes may be defined as follows:

Aryl is a non-substituted, mono-substituted, di-substituted or tri-substituted phenyl group, e.g. phenylene, n is 0 or 1, Aryl is an optionally substituted nitrogen-containing heteroaryl group such as, but not limited to, pyrid-4-yl, pyrid-3-yl or pyrid-2-yl, e.g. pyrid-3-ylene or pyrid-2-ylene, $R_0$ is hydrogen or a nitrogen-protecting group, in particular a nitrogen-containing heteroaryl group such as, but not limited to, pyrid-4-yl, pyrid-3-yl or pyrid-2-yl; and $R_3$ is halogen, methyl, methoxy, ethoxy, phenyl, trifluoromethyl, amino, heteroaryl or cyano.

Of particular interest is the sub-class of derivatives represented by the above structural formula (III) wherein $R_0$ is heteroarylmethyl or heteroarylethyl, and wherein heteroaryl is a nitrogen-containing group such as, but not limited to, pyrid-4-yl, pyrid-3-yl, pyrid-2-yl or benzimidazolyl.

The derivatives represented by the above structural formulae (I) or (II) or (III) may be in the form of a pharmaceutically acceptable salt. The latter include any therapeutically active non-toxic addition salt which compounds represented by the structural formula (I) or (II) or (III) are able to form with a salt-forming agent. Such addition salts may conveniently be obtained by treating the said derivative of the invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutanedioic, 2-hydroxy-1,2,3-propane-tricarboxylic and cyclohexanesulfamic acids and the like.

The derivatives of the structural formula (I) or (II) or (III) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylenediamine, N-methylglucamine, procaine and the like.

Reaction conditions for treating the derivatives having the structural formula (I) or (II) or (III) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the derivative of this invention.

According to a second aspect, the present invention relates to a method for producing 1-substituted-7-azabicyclo[2.2.1] heptyl derivatives represented by the structural formula (II) wherein $R_1$ is hydrogen and $R_2$ is hydroxyl, comprising reacting a 1-formyl-7-$R_0$-substituted-7-azabicyclo[2.2.1]-heptane, wherein $R_0$ is as defined in the structural formula (II), with an optionally substituted aryl iodide, bromide or chloride represented by the structural formula Y-Aryl-$(R_3)_n$ wherein Y is iodo, bromo or chloro, and wherein Aryl, n and $R_3$ are as defined in the structural formula (II).

Representative examples of optionally substituted aryl iodides, chlorides or bromides, wherein said aryl is homocyclic, suitable for this reaction include commercially available products such as, but not limited to:

non-substituted aryl iodides, aryl chlorides or aryl bromides, e.g. 1-iodonaphthalene, 1-chloronaphthalene, 1-bromonaphthalene, 2-bromonaphthalene, bromobenzene, chlorobenzene and iodobenzene;

mono-substituted phenyl iodides, phenyl chlorides or phenyl bromides, e.g. 2-chlorotoluene, 3-chlorotoluene, 4-chlorotoluene, 2-bromotoluene, 3-bromotoluene, 4-bromotoluene, 2-iodotoluene, 3-iodotoluene, 4-iodotoluene, 2-bromocumene, 3-bromocumene, 4-bromocumene, 2-chlorocumene, 3-chlorocumene, 4-chlorocumene, 4-iodocumene, 4-bromophenetole, 3-bromophenetole, 2-bromophenetole, 4-iodophenetole, 4-bromoanisole, 3-bromoanisole, 2-bromoanisole, 3-bromothioanisole, 2-bromothioanisole, 2-iodothioanisole, 3-iodothioanisole, 4-iodothioanisole, 4-n-butoxybromo-benzene, 4-tert-butoxybromobenzene, 2-(trifluoromethoxy)bromobenzene, 3-(trifluoromethoxy)bromobenzene, 4-(trifluoromethoxy)bromobenzene, 2-(trifluoromethoxy)iodobenzene, 3-(trifluoromethoxy)iodobenzene, 4-(trifluoro-methoxy)iodobenzene, bromo-3-isopropoxybenzene, 2-(2-bromophenyl)-pyridine and 1-(3-bromophenyl)isoquinoline; and poly-substituted phenyl iodides, phenyl chlorides or phenyl bromides, e.g. 2-bromo-m-xylene, 2-bromo-p-xylene, 3-bromo-o-xylene, 4-bromo-o-xylene, 4-bromo-m-xylene, 5-bromo-m-xylene, 2-chloro-m-xylene, 2-chloro-p-xylene, 4-chloro-o-xylene, 2,3-dichlorotoluene, 2,4-dichlorotoluene, 2,5-dichloro-toluene, 2,6-dichlorotoluene, 3,4-dichlorotoluene, 2,5-dibromotoluene, 3,5-dibromotoluene, 2-bromo-5-chlorotoluene, 3-bromo-4-fluorotoluene, 4-bromo-2-fluorotoluene, 5-bromo-2-fluorotoluene, 2-chloro-4-fluorotoluene, 2-chloro-6-fluorotoluene, 4-chloro-2-fluorotoluene, 2-fluoro-4-iodotoluene, 3,5-dichloro-cumene, 2,4-dichlorocumene, 4-amino-2-bromocumene, 2,4-dibromoanisole, 2,6-dibromoanisole, 3,5-dibromoanisole, 4-bromo-3-methylanisole, 4-bromo-2-methylanisole, 1-bromo-3,5-dimethoxybenzene, 1-bromo-2,4-dimethoxybenzene, 1-bromo-2,4,6-trimethoxybenzene, 1-bromo-3,4,5-trimethoxybenzene, 4-bromo-2,6-dimethylanisole, 2,4,6-tribromoanisole, 3-bromo-4-chloroanisole, 4-bromo-3-chloroanisole, 2-bromo-3-fluoroanisole, 2-bromo-4-fluoroanisole, 2-bromo-5-fluoroanisole, 2-bromo-6-fluoroanisole, 3-bromo-4-fluoroanisole, 3-bromo-5-fluoroanisole, 4-bromo-2-fluoroanisole, 4-bromo-3-fluoroanisole, 3,5-dibromothioanisole and 1-bromo-3,4-dimethoxybenzene.

Representative examples of optionally substituted aryl iodides or bromides or chlorides wherein said aryl is heterocyclic (e.g. heteroarylene), suitable for this reaction include commercially available products such as, but is not limited to, 3-chloropyridine, 2-chloropyridine, 2,3-dichloropyridine, 3-chloro-5-methyl-pyridine, 3-chloro-6-methylpyridine, 4-chloro-3-methylpyridine, 2-chloro-4-methylpyridine, 2-chloro-3-amino-4-methylpyridine, 3-chloro-6-phenylpyridine, 5-chloro-2-phenylpyridine, 2-amino-6-chloro-3-phenylpyridine, 2-chloro-3-cyano-6-phenylpyridine, 2-chloro-5-fluoro-3-methylpyridine, 2-bromopyridine, 3-bromopyridine, 4-bromopyridine, 5-bromopyrimidine, 3-bromoquinoline, 4-bromo-3-methylpyrazole, 2-bromothiazole, 2,5-dibromopyridine, 2,6-dibromo-pyridine, 3,4-dibromopyridine, 3,5-dibromopyridine, 3-bromo-2-chloropyridine, 5-bromo-2-chloropyridine, 2-bromo-5-chloropyridine, 2-chloro-3,5-dibromo-pyridine, 2-fluoro-3,5-dibromo-pyridine, 5-bromo-2-fluoropyridine, 3,5-dibromo-2-iodopyridine, 2-bromo-6-methoxy-pyridine, 5-bromo-2-methoxypyridine, 2-bromo-6-ethoxypyridine, 2-bromo-3-methylpyridine, 3-bromo-4-methylpyridine, 2-bromo-4-methylpyridine, 2-bromo-5-methylpyridine, 6-bromo-2-picoline, 5-bromo-2-picoline, 2-bromo-4-ethyl-pyridine, 2-bromo-5-cyanopyridine, 5-bromonicotonitrile, 5-bromo-2-(dimethylamino)pyridine, 2-bromo-3-phenyl-pyridine, 2-bromo-4-phenyl-pyridine, 2-bromo-5-phenylpyridine, 2-bromo-6-phenylpyridine, 3-bromo-2-phenyl-pyridine, 3-bromo-4-phenylpyridine, 3-bromo-5-phenylpyridine, 4-bromo-3-phenylpyridine, 5-bromo-2-phenylpyridine, 2-bromo-5-(trifluoromethyl)pyridine, 2-bromo-6-(trifluoromethyl)pyridine, 3-bromo-5-(trifluoromethyl)pyridine, 5-bromo-2-(trifluoromethyl)pyridine, tert-butyl 5-bromo-pyridine-2-carboxylate, 2-amino-6-bromopyridine, 2-amino-3-bromopyridine, 2-amino-5-bromopyridine and 3-amino-6-bromopyridine.

According to a specific embodiment of the present invention, the above method for producing 1-substituted-7-azabicyclo[2.2.1]heptyl derivatives represented by the structural formula (II) wherein $R_1$ is hydrogen and $R_2$ is hydroxyl may start from a 1-formyl-7-$R_0$-substituted-7-azabicyclo[2.2.1]-heptane wherein $R_0$ is not hydrogen, i.e. wherein the substituent $R_0$ acts as a N-protecting group, in which case the method may further comprise a step of cleaving off the N-protecting $R_0$ substituent to produce a derivative represented by the structural formula (II) wherein $R_0$ is hydrogen.

According to another embodiment, the present invention relates to a method for producing 1-substituted-7-azabicyclo[2.2.1]heptyl derivatives represented by the structural formula (II), wherein $R_1$ in combination with $R_2$ is oxo, comprising reacting a 1-cyano-7-$R_0$-substituted-7-azabicyclo[2.2.1]-heptane, wherein $R_0$ is as defined in the structural formula (II), with an optionally substituted aryl iodide, aryl chloride or aryl bromide represented by the structural formula Y-Aryl-$(R_3)_n$, wherein Y is iodo, chloro or bromo, and wherein Aryl, n and $R_3$ are as defined in the structural formula (II). Representative examples of optionally substituted aryl iodides, aryl chlorides or aryl bromides, wherein Aryl is an optionally substituted aryl or heteroaryl group, and being suitable for this reaction are as defined in details hereinabove.

According to a specific embodiment of the present invention, the above method for producing 1-substituted-7-azabicyclo[2.2.1]heptyl derivatives represented by the structural formula (II) wherein $R_1$ in combination with $R_2$ is oxo may start from a 1-cyano-7-$R_0$-substituted-7-azabicyclo[2.2.1]-heptane wherein $R_0$ is not hydrogen, i.e. wherein the substituent $R_0$ acts as a N-protecting group, in which case the method may further comprise a step of cleaving off the N-protecting $R_0$ substituent to produce a derivative represented by the structural formula (II) wherein $R_0$ is hydrogen.

According to another aspect, the present invention relates to a method for producing 1-substituted-7-azabicyclo[2.2.1] heptyl derivatives represented by the structural formula (I), comprising submitting a 1-aminomethyl-7-$R_0$-substituted-7-azabicyclo[2.2.1]-heptane, wherein $R_0$ is as defined in the structural formula (I), to a reaction step with an optionally substituted aryl iodide, aryl chloride or aryl bromide represented by the structural formula Y-Aryl-$(R_3)$, wherein Y is iodo, chloro or bromo, and wherein Aryl, n and $R_3$ are as defined in the structural formula (I). Preferably, said reaction step is a Buchwald-Hartwig cross-coupling reaction. This type of reaction is well known to the person skilled in the art and may be performed in the presence of a catalytic amount of a palladium complex catalyst. Suitable examples of palladium complex catalysts for this purpose include complexes wherein palladium is coordinated with monodentate ligands selected from the group consisting of chloro and triarylphosphines (e.g. triphenylphosphine and tri-(o-tolyl)phosphine), and/or bidentate ligands such as, but not limited to:

2,2'-bis-(diphenylphosphino)-1,1'-binaphthyl (BINAP),
1,3-bis-(diphenylphosphino)-propane (DPPP),
1,1'-bis-(diphenylphosphino)-ferrocene (DPPF), and
di-t-butyl-{1-[2-(dicyclohexylphosphanyl)ferrocenyl]ethyl}phosphine (DFEP).

According to a specific embodiment of the present invention, the above method for producing 1-substituted-7-azabicyclo[2.2.1]heptyl derivatives represented by the structural formula (I) may start from a 1-aminomethyl-7-$R_0$-substituted-7-azabicyclo[2.2.1]-heptane wherein $R_0$ is not hydrogen, i.e. wherein the substituent $R_0$ acts as a nitrogen-protecting group, in which case the method may further comprise a step of cleaving off the nitrogen-protecting $R_0$ substituent to produce a derivative represented by the structural formula (I) wherein $R_0$ is hydrogen. 1-aminomethyl-7-$R_0$-substituted-7-azabicyclo[2.2.1]-heptanes wherein $R_0$ is not hydrogen may already be known in the art, or may be produced by reducing, according to methods well known in the art (e.g. aluminium lithium hydride at low temperatures) the nitrile group of a 1-cyano-7-$R_0$-substituted-7-azabicyclo[2.2.1]-heptane already known in the art or that may be produced by a method disclosed herein.

For performing one of the above methods, it may first be necessary to produce 1-formyl-7-$R_0$-substituted-7-azabicyclo[2.2.1]-heptanes or 1-cyano-7-$R_0$-substituted-7-azabicyclo[2.2.1]-heptanes, wherein $R_0$ is selected from the group consisting of hydrogen, benzyl, heteroarylmethyl, heteroarylethyl, phenylethyl, naphthylmethyl, naphthylethyl, butoxycarbonyl, $C_{3-4}$ alkenyl and $C_{1-8}$ alkyl, and wherein said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl.

An exemplary but non-limiting method for producing a 1-cyano-7-$R_0$-substituted-7-azabicyclo[2.2.1]-heptane with the structural formula

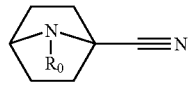

comprises reacting 4-methanesulfonylcyclohexanone with a primary amine $R_0NH_2$, e.g. a molar equivalent or a molar excess thereof, wherein $R_0$ is selected from the group consisting of benzyl, heteroarylmethyl, heteroarylethyl, phenylethyl, naphthylmethyl, naphthylethyl, butoxycarbonyl, $C_{3-4}$ alkenyl and $C_{1-8}$ alkyl, and wherein said benzyl is optionally substituted with 1 to 3 substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl, and at least two molar equivalents of acetone cyanohydrin, and optionally in the further presence of at least one molar equivalent of a tertiary amine such as, but not limited to, triethylamine in order to trap the methylsulfonic acid formed by the reaction.

Production of 4-methanesulfonylcyclohexanone itself is illustrated in a following example.

Reducing, according to methods well known in the art (e.g. aluminium lithium hydride at low temperatures) the nitrile group of a 1-cyano-7-$R_0$-substituted-7-azabicyclo[2.2.1]-heptane with the structural formula

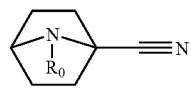

affords a compound of the invention represented by the structural formula (III) which is of particular interest when $R_0$ is heteroarylmethyl or heteroarylethyl and said heteroaryl is a nitrogen-containing group. This particular interest stems from the fact that the compound shows biological activity without a need for further derivatisation of the aminomethyl side group and without a need deprotection of the nitrogen atom of the azabicyclic ring.

A non-limiting method for producing a 1-formyl-7-$R_0$-substituted-7-s azabicyclo[2.2.1]-heptane is by the partial reduction of a 1-cyano-7-$R_0$-substituted-7-azabicyclo[2.2.1]-heptane with the structural formula

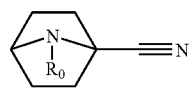

according to reducing methods well known in the art followed by acidic hydrolysis.

In all of the above methods when $R_0$ is originally present as a nitrogen-protecting group to be later converted into hydrogen by a suitable deprotection method in the usually final step of the production method, i.e. when $R_0$ is not a nitrogen-containing heteroarylmethyl or heteroarylethyl group providing desirable biological activity by itself, the proper selection of $R_0$ will take into is account both:

the capacity to allow for ring closure to form the bicyclic skeleton with a reasonable kinetics (such capacity being linked to parameters such as electron-withdrawing capacity and steric hindrance), and the easiness of removal in the usually final deprotection step.

Deprotection techniques for nitrogen-protecting groups, in particular for benzyl, mono-substituted benzyl and di-substituted benzyl groups, are well known in the art and are detailed for instance by Kocienski, *Protecting groups*, 3$^{rd}$ edition (2004), Georg Thieme Verlag, Stuttgart and by Greene et al in *Greene's protective groups in organic synthesis*, 4$^{th}$ edition (2007), Wiley-Interscience, New Jersey.

In order to suitably use a compound disclosed in this invention or a pharmaceutically acceptable salt, or solvate thereof, for the therapeutic treatment (including prophylactic treatment) of mammals including humans, it is usually formulated in accordance with standard pharmaceutical practice as a pharmaceutical composition including one or more appropriate pharmaceutically acceptable excipients.

The term "pharmaceutically acceptable carrier or excipient" as used herein in relation to pharmaceutical compositions and combined preparations means any material or substance with which the active principle, i.e. the derivative of the structural formula (I) or (II) or (III) may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutylnaphthalenesulphonic acid or a naphthalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphosphatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl group (e.g. cetyl, lauryl, palmityl, myristyl, oleyl and the like) and, as further substituents, unsubstituted or halogenated lower alkyl, benzyl and/or hydroxy-$C_{1-4}$ alkyl groups.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkylammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions of the present invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

In another aspect the present invention relates to a method of preventing or treating a disease, comprising the administration of a therapeutically effective amount of a derivative being represented by any one of the structural formulae (I), (II) and (III), including any one of the specific embodiments disclosed herein-above, in particular to a patient in need thereof, optionally in combination with one or more pharmaceutically acceptable carriers as described hereinabove. In particular the 1-substituted-7-azabicyclo[2.2.1]heptyl derivatives described herein are useful in modulating cholinergic function or nicotinic acetylcholine receptor activity. Numerous diseases, especially those mediated by a Nicotinic Acetylcholine Receptor or another receptor belonging to the Cys-loop superfamily of receptors, may be treated by means of a 1-substituted-7-azabicyclo[2.2.1]heptyl derivative such as disclosed herein.

Non-limiting examples of such diseases include, in addition to the previously mentioned CNS and neurological disorders, various forms of the inflammatory bowel disease (including, but not limited to, ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amylotropic lateral sclerosis, cognitive dysfunction, hypertension, bulimia, anorexia, obesity, cardiac arrythmia, gastric acid hypersecretion, ulcers, pheochromocytoma, progressive supramuscular palsy, chemical dependencies and addictions (e.g. dependencies on, or addictions to, nicotine (and/or tobacco products), alcohol, benzodiazepines, barbiturates, opioids or cocaine), headache, stroke, traumatic brain injury, obsessive-compulsive disorders, psychosis, Huntington's Chorea, tardive dyskinesia, hyperkinesia, dyslexia, schizophrenia, multi-infarct dementia, age-related cognitive decline, epilepsy, senile dementia of the Alzheimer's type, Parkinson's disease, attention deficit hyperactivity disorder (ADHD) and Tourette's Syndrome.

The compounds of this invention may also be used in combination with:
- one or more antidepressant drugs such as, but not limited to, tricyclic antidepressants and serotonin re-uptake inhibiting antidepressants, in order to treat both the cognitive decline and depression associated with Alzheimer's Disease, Parkinson Disease, or traumatic brain injury; and/or
- one or more muscarinic agonists in order to stimulate both central muscarinic and nicotinic receptors for the treatment, for example, of cognitive dysfunction, age-related cognitive decline, Alzheimer's Disease, Parkinson Disease, stroke or Huntington's Chorea; and/or
- one or more neurotrophic factors such as NGF in order to maximize cholinergic enhancement for the treatment, for example, cognitive dysfunction, age related cognitive decline, Alzheimer's Disease, Parkinson Disease, stroke or Huntington's Chorea; and/or
- one or more agents that slow or arrest Alzheimer's Disease such as, but not limited to, cognition enhancers, amyloid aggregation inhibitors, secretase inhibitors, tau kinase inhibitors, neuronal anti-inflammatory agents and estrogen-like therapeutic agents.

The precise biological activity profile of the 1-substituted-7-azabicyclo[2.2.1]heptyl derivatives disclosed in this invention may be determined by using one or more of the assays described in the review article published by Dunlop et al in *Biochemical Pharmacology* (2007) 74:1172-1181 such as, but not limited to:
- assays using a cell system wherein the alpha-7-subunit of the Nicotinic Acetylcholine Receptor complex is heterologously expressed, e.g. *Xenopus* (frog) *oocytes* or GH4C1 (mammalian) cells; or
- a radioactive displacement binding assay, e.g. using 3H labelled epibatidine and the *Xenopus oocyte* expression system; or
- a functional cell based binding assay (e.g. the Ca2+ flux FLIPR assay) wherein (*Xenopus*/GH4C1) a ligand gated ion channel consisting out of 5 alpha-7-subunits (pentamer) is formed in a cell system; in such assays, binding of a ligand causes ion fluxes which can be measured using fluorescent labelled ions e.g. through the "Fluorescent Imaging Plate Reading (FLIPR)" technique; this approach provides, next to the fact that a ligand binds to a receptor, also information with respect to the receptor activity; or
- electrophysiological recording such as the Two Electrode Voltage Clamp technique (TEVC), e.g. used with the radioligand binding assay and the *Xenopus* cell system, or the Patch Clamp technique, e.g. in combination with the "U-tube bathing technique"; or
- any one of the more specific binding assays disclosed in the following examples, or
- any one of the assays and methodologies disclosed by Broad et al in *J. Pharmacol. Exper. Therap.* (2006) 318: 1108-1117.

In order to suitably use the 1-substituted-7-azabicyclo [2.2.1]heptyl derivatives disclosed in this invention for therapeutic or prophylactic purpose, such compounds are preferably administered in a therapeutically effective amount (e.g. an analgesic dose when the pathologic condition to be treated is pain), e.g. a daily dose in the range of, for example, 0.1 mg to 75 mg per kg body weight is received, said daily dose being given if required in divided subdoses, also depending upon the patient to be treated and the severity of the disease to be cured. In general, lower doses will be administered when a parenteral route is employed. Thus, for example, for intravenous administration, a dose in the range of, for example, 0.5 mg to 30 mg per kg body weight will preferably be used. Similarly, for administration by inhalation, a dose in the range of, for example, 0.5 mg to 25 mg per kg body weight will preferably be used. According to a particular embodiment, the envisaged administration route for the compounds of the invention is oral administration, particularly in tablet form. Typically, unit dosage forms will contain about 1 mg to 500 mg of a compound of this invention.

The following examples are merely illustrative of the production and characterization of some 1-substituted-7-azabicyclo[2.2.1]heptyl derivatives of the present invention, but any type of compounds represented by the structural formulae (I) or (II) or (III) may be produced in accordance with the synthetic procedures described herein.

Purification and characterization of the compounds was performed by means of the following techniques and devices:

High resolution $^1$H-NMR (300 MHz) and $^{13}$C-NMR (75 MHz) spectra were run on a Jeol JNM-EX 300 NMR device. Peak assignments were obtained with the aid of DEPT, 2D-HSQC, 2D-COSY spectra. The compounds were diluted in deuterated solvents as indicated for each compound;

Low resolution mass spectra were recorded on an Agilent 1100 Series VS (ES, 4000V) mass spectrometer;

IR-spectra were obtained from a Perkin Elmer Spectrum One infrared spectrometer. Spectra of liquid compounds were collected by preparing a thin film between two sodium chloride plates. Crystalline compounds were mixed with potassium bromide and pressed until a transparent potassium bromide plate was obtained;

purification of reaction mixtures was performed by flash chromatography using a glass column with silica gel (commercially available from Acros, particle size 0.035-0.070 mm, pore diameter 6 nm);

Melting points of crystalline compounds were measured with a Büchi 540 apparatus.

EXAMPLE 1

Synthesis of 4-methanesulfonylcyclohexanone

Synthesis proceeds as shown in scheme 1. Starting from the commercially available protected cyclohexanone 6, the keto function was reduced with lithium aluminium hydride, followed by the activation of the hydroxyl function as the corresponding mesylate. After deprotection of the acetal 8, the desired precursor was obtained.

Scheme 1

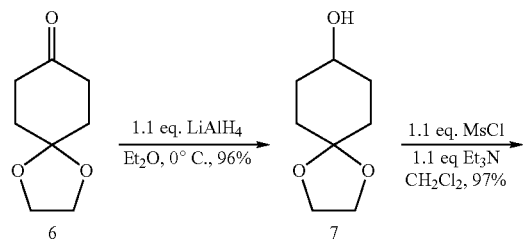

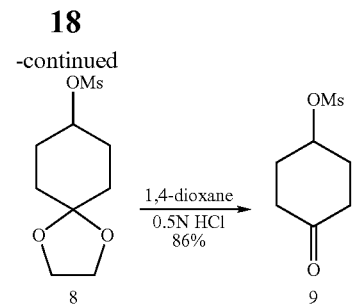

Details of these three steps are as follows:

Synthesis of Compound 7
(1,4-dioxaspiro[4.5]decan-8-ol)

In a dry 250 ml flask 2.5 g (68.5 mmole) LiAlH$_4$ was suspended in 20 ml dry diethyl ether. The flask was placed under inert N$_2$-atmosphere and cooled to 0° C. Then 10.4 g (66.6 mmole) 1,4-dioxaspiro[4.5]decan-8-one 6 was dissolved in 100 ml dry diethyl ether and slowly added to the suspension. The reaction mixture was stirred for 30 minutes at room temperature. Water, diluted with THF, was added in order to remove the excess LiAlH$_4$. The reaction mixture was filtrated over MgSO$_4$ and the volatile components were removed by evaporation.

Synthesis of Compound 8
(8-methanesulfonyl-1,4-dioxaspiro[4.5]decane)

In a 250 ml flask 10.36 g (65.5 mmole) 1,4-dioxaspiro[4.5]decan-8-ol 7 and 7.31 g (72.2 mmole) triethylamine were dissolved in 80 ml CH$_2$Cl$_2$. The flask was cooled to 0° C. and a solution of 8.27 g (72.2 mmole) methanesulfonyl chloride in 20 ml CH$_2$Cl$_2$ was slowly added. Afterwards the cooling system was removed and the reaction mixture was left under agitation for 24 hours. Triethylamine hydrochloride crystals precipitated during this period. 200 ml saturated NaHCO$_3$ solution was added and compound 8 was extracted three times with dichloromethane. The combined organic phases were dried over MgSO$_4$, solids were filtered off and the volatile components were evaporated.

Synthesis of Compound 9
(4-methanesulfonylcyclohexanone)

15.36 grams (65 mmole) of 8-methanesulfonyl-1,4-dioxaspiro[4.5]decane 8 was dissolved in 300 ml 1,4-dioxane and added to 300 ml 0.5M HCl. After stirring for 48 hours the pH was set to 8 using a 2M solution of KOH. The reaction mixture was extracted three times with CH$_2$Cl$_2$. The combined extracts were washed 4 times with a saturated NaHCO$_3$ solution and dried over MgSO$_4$. After filtration of the solids and evaporation of the volatile components, compound 9 was obtained as a slightly yellow solid.

EXAMPLE 2

Synthesis of 7-R-substituted-7-azabicyclo[2.2.1]heptyl-1-carbonitriles

The key step involves the one-pot procedure of imine formation, addition of cyanide to the imine function, followed by intramolecular nucleophilic substitution, as shown in scheme 2. This was performed by treating, in a closed vessel in methanol for two days, the mesyloxyketone 9 with at least one molar equivalent (compound 10a), preferably two or three molar equivalents (compounds 10b-10f) of the relevant primary amine and two equivalents of acetone cyanohydrine, and optionally (compound 10a) in the further presence of at least one molar equivalent of triethylamine in order to trap the methylsulfonic acid formed. The conversion of the mesyloxyketone 9 to each 7-azabicyclo[2.2.1]hexane-1-carbonitrile 10 was complete, however the purification of the resulting compound by flash chromatography (or by crystallisation of the hydrochloride salt in case of compound 10a) lowers the reaction yield. Compounds 10a-10f exhibit a high affinity for silica gel, leading to some product loss during purification. Six illustrative substituted 7-azabicyclo[2.2.1]heptane-1-carbonitriles were obtained. This method proves to be superior to the method of Grygorenko et al (cited supra) since no evidence of isomer formation could be found.

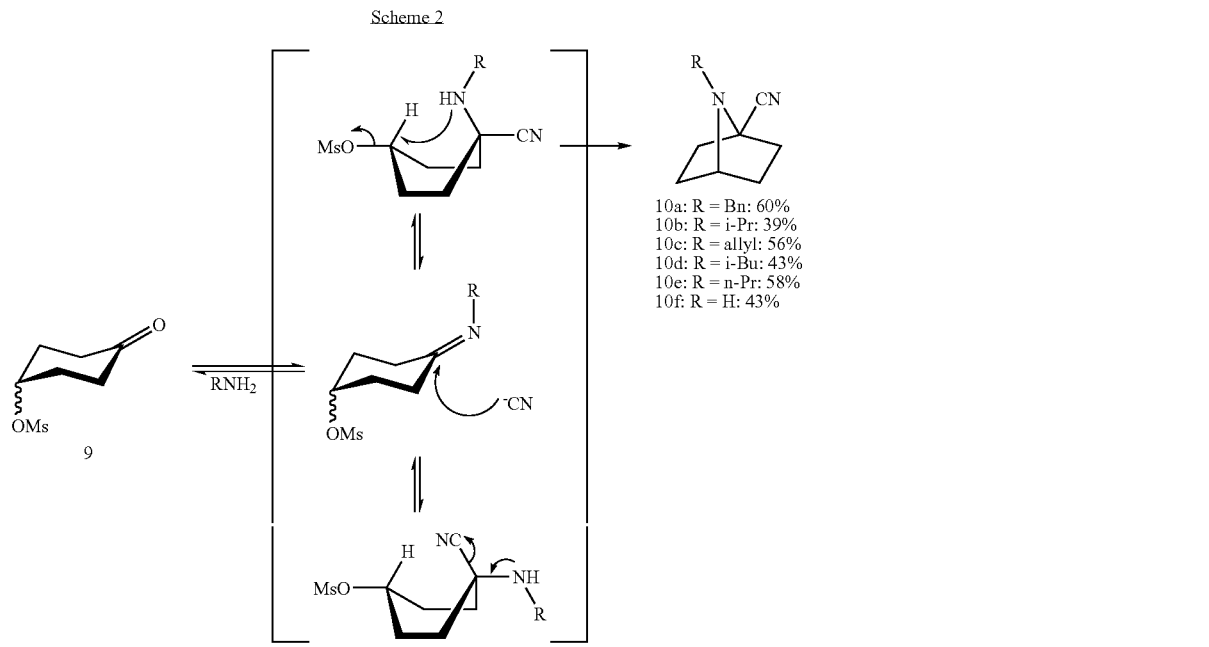

Scheme 2

10a: R = Bn: 60%
10b: R = i-Pr: 39%
10c: R = allyl: 56%
10d: R = i-Bu: 43%
10e: R = n-Pr: 58%
10f: R = H: 43%

Details of these syntheses are as follows:

Synthesis of Compound 10a (7-benzyl-7-azabicyclo[2.2.1]heptyl-1-carbonitrile)

In a dry, pressure resistant vessel of 20 ml, 1.25 g (6.5 mmole) 4-methanesulfonylcyclohexanone 9, 0.70 g (6.5 mmole) benzylamine, 1.11 g (13 mmole) acetone cyanohydrine and 1.32 g (13 mmole) triethylamine were dissolved in 16 ml dry methanol. The vessel was closed and heated to 100° C. for 50 hours. Methanol was evaporated and the residue was re-dissolved in dichloromethane. The solution was washed with a saturated NaHCO$_3$ solution and dried over MgSO$_4$. After filtration of the solids the volatile components were evaporated. Chromatography yielded 60% 7-benzyl-7-azabicyclo[2.2.1]heptyl-1-carbonitrile 10a as a yellow oil which was characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, CDCl$_3$) (ppm): 1.33-1.44 (2H, m, 2×CH$_a$H$_b$CH); 1.77-1.95 (4H, m, 2×CH$_a$H$_b$CH, 2×C H$_a$H$_b$C$_q$); 2.09-2.22 (2H, m, 2×CH$_a$H$_b$C$_q$); 3.26 (1H, t, J=4.4 Hz, CH$_2$CHCH$_2$); 3.64 (2H, s, NCH$_2$Ph); and 7.22-7.40 (5H, m, 5×CH, Ph.);

$^{13}$C-NMR (75 MHz, CDCl$_3$) (ppm): 27.96 (2×CH$_2$CH); 34.37 (2×CH$_2$C$_q$); 50.38 (NCH$_2$Ph); 58.43 (CH$_2$CHCH$_2$); 59.53 (N—C$_q$); 120.33 (C≡N); 127.23 (CH, Ph.); 128.36 (CH, Ph.); 128.67 (CH, Ph.); and 138.74 (C$_q$, Ph.);

IR (cm$^{-1}$): 2240 (C≡N); and

MS$^{ES}$ m/z (%): 213 (M+H$^+$, 100); 91 (15).

Synthesis of Compounds 10b-f

In a dry, pressure resistant vessel of 20 ml, 1.25 g (6.5 mmole) 4-methanesulfonylcyclohexanone 9, 19.5 mmole of the relevant amine and 1.11 to g (13 mmole) acetone cyanohydrine were dissolved in 16 ml dry methanol. The vessel was closed and heated to 100° C. for 50 hours. Methanol was evaporated and the residue was re-dissolved in dichloromethane. The solution was washed with a saturated NaHCO$_3$ solution and dried over MgSO$_4$. After filtration of the solids the volatile components were evaporated. Chromatography achieved (yields as indicated in scheme 2) 7-hydrocarbyl-7-azabicyclo[2.2.1]heptyl-1-carbonitriles 10b-e and 7-azabicyclo[2.2.1]heptyl-1-carbonitrile 10f which were characterised by proton ($^1$H-NMR) and carbon ($^{13}$C-NMR) nuclear magnetic resonance, mass spectrum (MS$^{ES}$) and infrared (IR) spectrophotometry as follows:

Compound 10b (yield 39%)

$^1$H-NMR (300 MHz, CDCl$_3$) (ppm): 1.24 (6H, d, J=6.3 Hz, 2×CH$_3$); 1.34-1.47 (2H, m, 2×CH$_a$H$_b$CH); 1.75-1.91 (4H, m, 2×CH$_a$H$_b$CH, 2×CH$_a$H$_b$C$_q$); 2.09-2.21 (2H, m, 2×CH$_a$H$_b$C$_q$); 2.68 (1H, septet, J=6.3 Hz, CH$_3$CHCH$_3$); and 3.62 (1H, t, J=4.4 Hz, CH$_2$CHCH$_2$), $^{13}$C-NMR (75 MHz, CDCl$_3$) (ppm): 23.07 (2×CH$_3$); 28.17 (2×CH$_2$CH); 35.22 (2×CH$_2$C$_q$); 46.54 (CH$_3$CHCH$_3$); 57.09 (N—C$_q$); 59.00 (CH$_2$CHCH$_2$); and 121.78 (C≡N);

IR (cm$^{-1}$): 2238 (C≡N); and

MS$^{IE}$ m/z (%): 164 (M$^+$, 16); 149 (57); 108 (8); 94 (100) and 67(10).

Compound 10c (yield 56%)

$^1$H-NMR (300 MHz, CDCl$_3$) (ppm): 1.25-1.50 (2H, m, 2×CH$_a$H$_b$CH); 1.77-1.93 (4H, m, 2×CH$_a$H$_b$CH, 2×C H$_a$H$_b$C$_q$); 2.04-2.16 (2H, m, 2×CH$_a$H$_b$C$_q$); 3.14 (2H, br. d, J=5.8 Hz, NCH$_2$); 3.47 (1H, t, J=4.5 Hz, CH$_2$CHCH$_2$); 5.12-5.30 (2H, m, CH=CH$_2$); and 5.92 (1H, dxdxt, J$_1$=17.2 Hz, J$_2$=10.1 Hz, J$_3$=6.3 Hz, CH=CH$_2$);

$^{13}$C-NMR (75 MHz, CDCl$_3$) (ppm): 27.98 (2×CH$_2$CH); 34.23 (2×CH$_2$C$_q$); 49.42 (NCH$_2$); 58.61 (CH$_2$CHCH$_2$); 59.21 (CH$_2$C$_q$CH$_2$); 117.47 (CH=CH$_2$); 120.18 (C≡N); and 135.21 (CH=CH$_2$);

IR (cm$^{-1}$): 2240 (C≡N) and 1644 (C=C);

MS$^{ES}$ m/z (%): 163 (M+H$^+$, 100) and 136 (12).

Compound 10d (yield 43%)

$^1$H-NMR (300 MHz, CDCl$_3$) (ppm): 0.95 (6H, d, J=6.6 Hz, 2×CH$_3$); 1.35-1.42 (2H, m, 2×CH$_a$H$_b$CH); 1.63-1.91 (5H, m, 2×CH$_a$H$_b$CH, 2×CH$_a$H$_b$C$_q$, NCH$_2$CH(CH$_3$)$_2$); 1.99-2.09 (2H, m, 2×CH$_a$H$_b$C$_q$); 2.24 (2H, d, J=7.2 Hz, NCH$_2$CH(CH$_3$)$_2$); and 3.40 (1H, t, J=4.4 Hz, CH$_2$CHCH$_2$);

$^{13}$C-NMR (75 MHz, CDCl$_3$) (ppm): 20.87 (2×CH$_3$); 28.20 (2×CH$_2$CH); 28.34 (NCH$_2$CH(CH$_3$)$_2$); 34.35 (2×CH$_2$C$_q$); 53.97 (NCH$_2$CH(CH$_3$)$_2$); 59.65 (CH$_2$CHCH$_2$); 59.92 (NC$_q$); and 120.80 (C≡N);

IR (cm$^{-1}$): 2241 (C≡N); and

MS$^{ES}$ m/z (%): 180 (M$^+$+2, 10) and 179 (M$^+$+1, 84).

Compound 10e (yield 58%)

$^1$H-NMR (300 MHz, CDCl$_3$) (ppm): 0.96 (3H, t, J=7.4 Hz, CH$_3$); 1.38-1.46 (2H, m, 2×CH$_a$H$_b$CH); 1.56 (2H, sextet, J=7.4 Hz, CH$_2$CH$_3$); 1.73-1.93 (4H, m, 2×CH$_a$H$_b$CH, 2×CH$_a$H$_b$C$_q$); 2.02-2.18 (2H, m, 2×CH$_a$H$_b$C$_q$); 2.44 (2H, t, J=7.7 Hz, NCH$_2$) and 3.48 (1H, t, J=4.4 Hz, CH$_2$CHCH$_2$);

$^{13}$C-NMR (75 MHz, CDCl$_3$) (ppm): 11.99 (CH$_3$); 22.55 (CH$_2$CH$_3$); 28.09 (2×CH$_2$CH); 34.20 (2×CH$_2$C$_q$); 48.13 (NCH$_2$); 58.89 (CH$_2$CHCH$_2$); 59.67 (NC$_q$) and 120.53 (C≡N);

IR (cm$^{-1}$): 2241 (C≡N); and

MS$^{ES}$ m/z (%): 166 (M$^+$+2, 17); 165 (M$^+$+1, 100); 138 (7).

Compound 10f (yield 43%)

$^1$H-NMR (300 MHz, CDCl$_3$) (ppm): 1.22-2.01 (8H, m, 4×CH$_a$H$_b$, 4×CH$_a$H$_b$); and 3.78 (1H, t, J=4.4 Hz, CH$_2$CHCH$_2$);

$^{13}$C-NMR (75 MHz, CDCl$_3$) (ppm): 30.59 (2×CH$_2$CH); 35.71 (2×CH$_2$C$_q$); 55.43 (NC$_q$); 57.46 (CH$_2$CHCH$_2$) and 121.07 (C≡N);

IR (cm$^{-1}$): 3207; 2243 (C≡N); and

MS$^{ES}$ m/z (%): 123 (M$^+$, 98); 106 (7).

EXAMPLE 3

Preparation of 1-substituted-7-benzyl-7-azabicyclo[2.2.1]heptyl derivatives

The sequential derivatisation of 7-hydrocarbyl-7-azabicyclo[2.2.1]heptyl-1-carbonitriles 10a-e was performed according to the methodology of scheme 3 below. In a first step, the illustrative compound 10a (7-benzyl-7-azabicyclo[2.2.1]heptyl-1-carbonitrile) was submitted to partial reduction, followed by acidic hydrolysis. Infrared analysis confirmed the reduction to the expected aldimine intermediate (not shown in scheme 3) which however was quite resistant to hydrolysis, chromatography being is needed to obtain the pure aldehyde derivative 11 in 49% yield. The subsequent addition of the 2-chloropyridyl group onto the aldehyde derivative provided the alcohol 12 in 91% yield.

Alternatively, the nucleophilic addition of the 2-chloropyridyl group was also performed directly onto the nitrile compound 10a. After acidic hydrolysis of the resulting imine intermediate (not shown in scheme 3), the ketone 13 was obtained in 73% yield.

Scheme 3

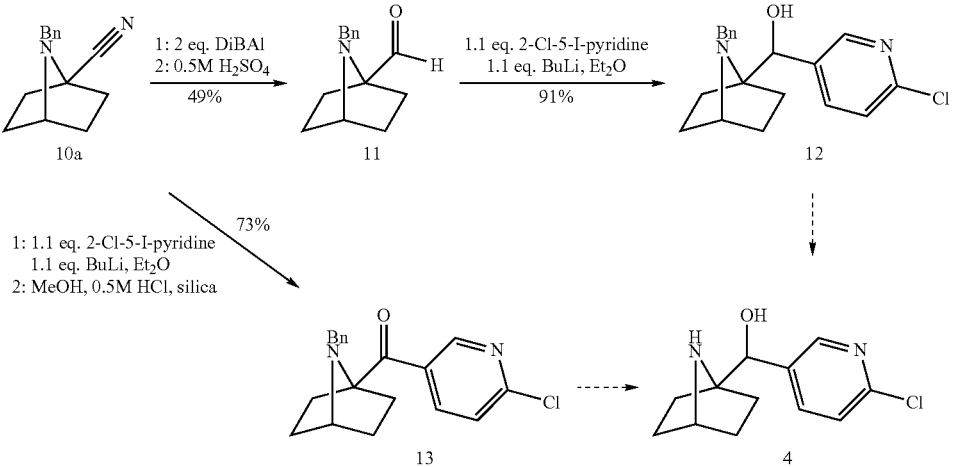

Synthesis of Compound 11 (7-benzyl-7-azabicyclo[2.2.1]heptyl-1-carbaldehyde)

In a dry 100 ml flask 0.7 g (3.3 mmole) 7-benzyl-7-azabicyclo[2.2.1]heptyl-1-carbonitrile was dissolved in 35 ml dry diethyl ether. The flask was placed under inert N$_2$-atmosphere and cooled to −78° C. With a syringe 6.6 ml of a 1M solution of diisobutyl aluminium hydride (DiBAl) (6.6 mmole) was added. The reaction mixture was stirred for one hour at −78° C. and 5 hours at 20° C. Then 0.49 g (6.6 mmole) ethyl formate was added. After 30 minutes stirring, 40 ml 0.5M H$_2$SO$_4$ was added, which was neutralised by means of 3M NaOH after 15 hours. The reaction mixture was extracted three times with diethyl ether and the combined organic phases were dried over MgSO$_4$. After filtration of the solids and removal of the volatile components, the resulting product (yield: 49%) was characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, CDCl$_3$) (ppm): 1.39-1.59 (4H, m, 2×CH$_{exo}$H$_{endo}$CH, 2×CH$_a$H$_b$C$_q$); 1.88-2.12 (4H, m, 2×C H$_{exo}$H$_{endo}$CH, 2×CH$_a$H$_b$C$_q$); 3.38 (1H, t, J=4.5 Hz, CH$_2$C$\overline{H}$CH$_2$); 3.51 (2H, s, NC$\overline{H_2}$Ph); 7.22-7.39 (5H, m, 5×C$\overline{H}$, Ph.) and 9.70 (1H, s, CO$\overline{H}$);

$^{13}$C-NMR (75 MHz, CDCl$_3$) (ppm): 28.46 (2×$\overline{CH_2}$CH); 29.84 (2×$\overline{CH_2}$C$_q$); 51.04 (N$\overline{CH_2}$Ph); 60.97 (C$\overline{H_2}$CHCH$_2$ ring); 76.14 ($\overline{CH_2}$C$_q$CH$_2$ ring); 127.31 ($\overline{CH}$, Ph.); 128.43 (2×$\overline{CH}$, Ph.); 128.98 (2×$\overline{CH}$, Ph.); 139.44 ($\overline{C_q}$, Ph.) and 202.85 ($\overline{C}$=O);

IR (cm$^{-1}$): 1722 (C=O); and

MS$^{ES}$ m/z (%): 234 (M+H$_3$O$^+$, 38) and 216 (M+H$^+$, 100).

Synthesis of Compound 12

In a dry 50 ml flask 1.1 g (4.6 mmole) 2-chloro-5-iodopyridine was dissolved in 30 ml dry diethyl ether. The flask was placed under inert N$_2$-atmosphere and cooled to −78° C. To this solution 1.84 ml of a 2.5M solution (4.6 mmole) of butyl lithium (BuLi) was added. After stirring 2.5 hours at −78° C. a solution of 0.90 g (4.2 mmole) 7-benzyl-7-azabicyclo[2.2.1]heptyl-1-carbaldehyde 11 in 10 ml dry diethyl ether was added. 30 minutes later the reaction mixture was allowed to heat up to 20° C. and left under agitation overnight. Methanol was added in order to neutralise the excess BuLi and the volatile components were is evaporated. The reaction mixture was re-dissolved in a minimal amount of dry diethyl ether. The volatile components were evaporated and the precipitated salts were filtered off (yield 91%) and characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, CDCl$_3$) (ppm): 0.82-0.95 (1H, m, C$_q$CH$_a$H$_b$C$_b$H$_2$); 1.15-1.25 (2H, m, 1×CHC$_b$H$_{exo}$H$_{endo}$, 1×C$_q$$\overline{CH}$$_a$H$_b$C$_a$H$_2$); 1.43-1.52 (1H, m, 1×CHC$_a$H$_{exo}$$\overline{H}_{endo}$); 1.56-1.65 (1H, m, 1×CHC$_b$H$_{exo}$H$_{endo}$); 1.80 (1H, txt, J$_1$=12.1 Hz, J$_2$=3.9 Hz, C$_q$CH$_a$H$_b$$\overline{C_a}$H$_2$); 1.96 (1H, txt, J$_1$=12.1 Hz, J$_2$=3.9 Hz, C$_q$$\overline{CH}$$_a$H$_b$$\overline{C_b}$H$_2$); 2.02-2.16 (1H, m, 1×CHC$_a$H$_{exo}$H$_{endo}$), 3.25 (1$\overline{H}$, t, J=4.7 Hz, CH$_2$CHCH$_2$); 3.40 (1H, d, $\overline{J}$=13.2 Hz, NCH$_a$H$_b$Ph); 3.61 (1H, br. s, OH); 3.85 (1H, d, J=13.2 Hz, NC$\overline{H}_a$H$_b$Ph); 4.99 (1H, s, CHOH); 7.23-7.44 (5H, m, 5×CH Ph.); 7.29 (1H, d, J=8.3 Hz, $\overline{C_q}$CHCH pyr.); 7.73 (1H, dd, J$_1$=8.3 Hz, J$_2$=2.4 Hz, C$_q$CHCH pyr.) and 8.36 (1H, d, J=2.4 Hz, C$_q$CHN pyr.);

$^{13}$C-NMR (75 MHz, CDCl$_3$) (ppm): 28.13 (C$_b$H$_2$CH$_2$); 28.58 (C$_b$H$_2$CH$_2$); 28.71 (C$_a$H$_2$CH$_2$); 29.78 ($\overline{C}_a$H$_2$CH$_2$); 48.88 (N$\overline{CH_2}$Ph); 60.17 ($\overline{CH_2}$CHCH$_2$); 70.98 ($\overline{CH}$OH); 72.78 (C$\overline{H_2}$C$_q$CH$_2$); 123.83 (C$_q$$\overline{CH}$CH pyr); 127.28 (1×CH, Ph.); 128.63 (4×CH, Ph.); 135.77 ($\overline{C_q}$ pyr.); 137.41 (C$_q$$\overline{CH}$CH pyr.); 139.47 ($\overline{C_q}$ Ph.); 148.16 ($\overline{C_q}$CHN pyr.) and 150.49 ($\overline{C_q}$Cl, pyr.);

IR (cm$^{-1}$): 3370 (OH);

MS$^{ES}$ m/z (%): 331 (M+H$^+$, 34); 329 (M+H$^+$, 100) and 274 (30).

Synthesis of Compound 13

In a dry 50 ml flask 1.1 g (4.6 mmole) 2-chloro-5-iodopyridine was dissolved in 30 ml dry diethyl ether. The flask was placed under inert N$_2$-atmosphere and cooled to −78° C. To this solution 1.84 ml of a 2.5M solution (4.6 mmole) of butyl lithium (BuLi) was added. After stirring 2.5 hours at −78° C. a solution of 0.89 g (4.2 mmole) 7-benzyl-7-azabicyclo[2.2.1]heptyl-1-carbonitrile in 10 ml dry diethyl ether was added. 30 minutes later the reaction mixture was allowed to heat up to 20° C. and left under agitation overnight. Methanol was added in order to neutralise the excess BuLi and the volatile components were evaporated. The reaction mixture was re-dissolved in 40 ml of a 1:1 mixture of methanol and 0.5M HCl. 0.5 g silica gel was added and the mixture was stirred for 24 hours at 20° C. The pH was adjusted to 8 by adding a concentrated NaHCO$_3$ solution. Compound 13 was extracted three times by means of dichloromethane and the combined organic phases were dried over MgSO$_4$. After filtration of the solids and evaporation of the volatile components, compound 13 (yield 73%) was further purified by crystallisation from methanol and was characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, CDCl$_3$) (ppm): 1.49 (2H, dxdxd, J$_1$=11.6 Hz, J$_2$=9.3 Hz, J$_3$=4.1 Hz, 2×CHCH$_{exo}$H$_{endo}$ of 2×C$_q$CH$_a$H$_b$); 1.65-1.85 (2H, br. s, 2×CHCH$_{exo}$$\overline{H}_{endo}$ of 2×C$_q$C$\overline{H}_a$H$_b$); 1.89-2.08 (2H, m, 2×CHCH$_{exo}$H$_{endo}$); 2.20-2.46 (2$\overline{H}$, br. s, 2×CHCH$_{exo}$H$_{endo}$ of 2×C$_q$$\overline{CH}_a$H$_b$); 3.39 (2H, s, NCH$_2$Ph); 3.42 (1H, t, J=4.7 Hz, CH$_2$C$\overline{H}$CH$_2$); 7.17-7.33 (5H, m, Ph.); 7.40 (1H, d, J=8.3 Hz, C$_q$CH$\overline{CH}$ pyr.); 8.71 (1H, dxd, J$_1$=8.3 Hz, J$_2$=2.3 Hz, C$_q$$\overline{CH}$CH pyr.); 9.73 (1H, d, J=2.3 Hz, CHN, Pyr.);

$^{13}$C-NMR (75 MHz, CDCl$_3$) (ppm): 25.7-30.1 (4×CH$_2$ ring); 50.06 (NCH$_2$Ph); 59.86 (CH$_2$CHCH$_2$); 77.56 ($\overline{CH_2}$C$_q$CH$_2$); 124.21 ($\overline{C_q}$CHCH pyr.); 127.27 (1×CH Ph.); 128.48 (2×CH Ph.); 128.60 (2×CH Ph.); 129.47 ($\overline{C_q}$, pyr.); 138.89 (C$_q$, Ph.); 139.93 (C$_q$CH$\overline{CH}$ pyr.); 152.34 ($\overline{CH}$N pyr.); 155.44 ($\overline{C_q}$Cl, pyr.) and 199.50 (CO);

IR (cm$^{-1}$): 1675 (C=O);

MS$^{ES}$ m/z (%): 329 (M+H$^+$, 41); 327 (M+H$^+$, 100); 323 (45) and 272 (80).

EXAMPLE 4

Preparation and derivatisation of 7-benzyl-7-azabicyclo[2.2.1]hept-1-yl)(pyridin-3-yl)methanone 14

The ketone 14 was synthesised from 7-azabicyclo[2.2.1]heptane-1-carbonitrile 10a in 48% yield as shown in scheme 4. Then, refluxing ketone 14 with ammonium formate in the presence of Pd/C led to the complete removal of the benzyl group within 4 hours and compound 15 was recovered after crystallisation from diethyl ether.

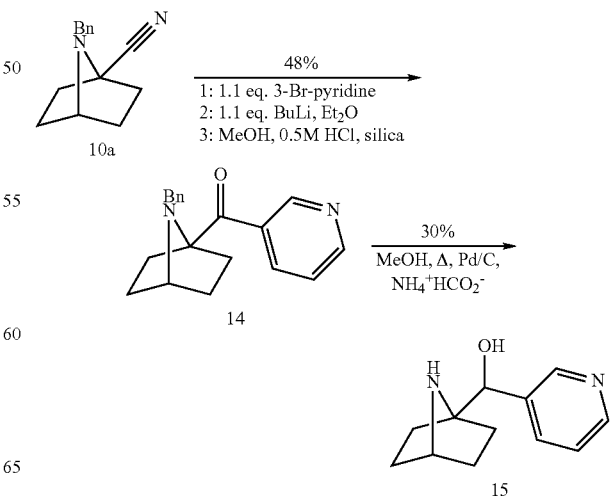

Scheme 4

Details of these syntheses are as follows:

Synthesis of Compound 14

In a dry 50 ml flask 1.05 g (5 mmole) 7-benzyl-7-azabicyclo[2.2.1]heptyl-1-carbonitrile 10a and 0.87 g (5.5 mmole) 3-bromopyridine were dissolved in 25 ml dry diethyl ether. The flask was placed under $N_2$-atmosphere and cooled to $-40°$ C. Using a syringe pump 2.2 ml of a 2.5M solution (5.5 mmole) butyl lithium (BuLi) was added over a period of 30 minutes. The reaction mixture was stirred for one hour at $-40°$ C. and then allowed to slowly heat up to $20°$ C. Methanol was added in order to neutralise the excess BuLi and the volatile components were evaporated. The reaction mixture was re-dissolved in 25 ml of a 1:1 mixture of methanol and 0.5M HCl. 0.5 g of silica gel was added and the mixture was stirred for 15 hours at room temperature. The pH was adjusted to 8 by adding a concentrated $NaHCO_3$ solution. Compound 14 was extracted three times by means of dichloromethane and the combined organic phases were dried over $MgSO_4$. After filtration of the solids and evaporation of the volatile components, compound 14 (yield 48%) was purified by means of column chromatography and was characterised by proton ($^1$H-NMR) and carbon ($^{13}$C-NMR) nuclear magnetic resonance, mass spectrum ($MS^{ES}$) and infrared (IR) spectrophotometry as follows:

$^1$H-NMR (300 MHz, $CDCl_3$) (ppm): 1.48 (2H, dxdxd, $J_1$=11.7 Hz, $J_2$=9.2 Hz, $J_3$=4.0 Hz, 2×$CHCH_{exo}H_{endo}$ of 2×$C_qCH_aH_b$ ring); 1.69-1.87 (2H, br. s, 2×$CHCH_{exo}\overline{H}_{endo}$ of 2×$C_q\overline{CH}_aH_b$ ring); 1.92-2.06 (2H, m, 2×$CHCH_{exo}\overline{H}_{endo}$); 2.26-2.40 (1H, m, 2×$CHCH_{exo}H_{endo}$ of $C_qCH_aH_b$ ring); 3.40 (2H, s, $NCHH_2Ph$); 3.41 (1H, t, J=4.5 Hz, $CH_2CHCH_2$); 7.18-7.30 (5H, m, 5×CH Ph.); 7.40 (1H, dxdxd, $J_1$=8.0 Hz, $J_2$=5.0 Hz, $J_3$=0.7 Hz, NCHCH pyr.); 8.75 (1H, dxd, $J_1$=5.0 Hz, $J_2$=2.0 Hz, NCHCH pyr.); 8.79 (1H, dxt, $J_1$=8.0 Hz, $J_2$=2.0 Hz, $C_qCHCH$ pyr.) and 9.89 (1H, dxd, $J_1$=2.0 Hz, $J_2$=0.7 Hz, $C_q\overline{CHN}$ pyr.);

$^{13}$C-NMR (75 MHz, $CDCl_3$) (ppm): 28.5-30.6 (4×$CH_2$ ring); 50.16 ($NCH_2Ph$); 59.63 ($CH_2CHCH_2$); 77.16 ($CDCl_3$); 77.59 ($CH_2C_q\overline{CH}_2$); 123.42 (NCHCH pyr.); 127.16 (1×CH Ph.); 128.40 (2×CH Ph.); 128.61 (2×CH Ph.); 130.70 ($C_q$ pyr.); 137.24 ($C_q\overline{CHCH}$); 139.15 ($C_q$ Ph.); 151.77 ($C_q\overline{CHN}$ pyr.); 153.36 (NCHCH pyr.) and 200.71 (CO);

IR ($cm^{-1}$): 1675 (C=O); and $MS^{ES}$ m/z (%): 293.2 ($M+H^+$, 100).

Synthesis of Compound 15

In a 50 ml flask 0.10 g (0.34 mmole) 7-benzyl-7-azabicyclo[2.2.1]hept-1-yl)(pyridin-3-yl)methanone 14 and 0.09 g (1.37 mmole) ammonium formate were dissolved in 20 ml methanol. To this solution 0.05 g (5% Pd) Pd/C was added and the suspension was refluxed 4 hours. The Pd/C catalyst was filtered off and methanol evaporated. Then 5 ml dichloromethane was added and the excess ammonium formate was filtered off. After evaporation of dichloromethane, the solid compound 15 (yield 30%) was further purified by crystallisation from diethyl ether and was characterised by proton ($^1$H-NMR) and carbon ($^{13}$C-NMR) nuclear magnetic resonance, mass spectrum ($MS^{ES}$), infrared (IR) spectrophotometry and melting point as follows:

$^1$H-NMR (300 MHz, $CDCl_3$) (ppm): 1.07 (1H, dxdxd, $J_1$=11.9 Hz, $J_2$=9.2 Hz, $J_3$=4.3 Hz, $C_qC_aH_aH_b$ ring); 1.13-1.25 (1H, m, $C_qC_bH_aH_b$ ring); 1.39-1.51 (2H, m, 2×$CHCH_{exo}H_{endo}$ ring); 1.57 (1H, txt, $J_1$=11.8 Hz, $J_2$=3.7 Hz, $C_qC_bH_a\overline{H}_b$ ring); 1.64-1.82 (2H, m, 2×$CHCH_{exo}H_{endo}$ ring); 1.89 (1H, txt, $J_1$=11.9 Hz, $J_2$=3.9 Hz, $C_qC_a\overline{H}_aH_b$ ring); 3.62 (1H, t, J=4.5 Hz, $CHCH_2$ ring); 3.79 (2H, br. s, OH+NH); 5.06 (1H, s, CHOH); 7.26 (1H, dxd, $J_1$=7.9 Hz, $J_2$=4.7 Hz, NCHCH pyr.); 7.76 (1H, dxt, $J_1$=7.9 Hz, $J_2$=1.7 Hz, $C_q\overline{CHCH}$ pyr.); 8.50 (1H, dxd, $J_1$=4.7 Hz, $J_2$=1.7 Hz, NCHCH pyr.) and 8.59 (1H, d, J=1.7 Hz, $NCHC_q$ pyr.);

$^{13}$C-NMR (75 MHz, $CDCl_3$) (ppm): 27.93 ($C_qC_aH_2$ ring); 31.08 (1×$CHCH_2$ ring); 31.45 (1×$CHCH_2$ ring); 32.73 ($C_qC_bH_2$ ring); 56.78 ($CHCH_2$ ring); 72.01 ($C_qCH_2$ ring); 73.31 (CHOH); 77.33 ($CDCl_3$); 123.25 (NCHCH pyr.); 134.44 ($C_q\overline{CHCH}$ pyr.); 137.70 ($C_q$ pyr.); 148.35 ($NCHC_q$ pyr.) and 148.86 (NCHCH pyr.);

IR ($cm^{-1}$): 3436 (OH or NH) and 3234 (OH of NH);

$MS^{ES}$ m/z (%): 205.2 ($M+H^+$, 100); and melting point: 139.5° C.

EXAMPLE 5

Preparation of 7-benzyl-7-azabicyclo[2.2.1]hept-1-ylmethyl)-pyridin-2-yl-amine

In a different approach, 7-hydrocarbyl-7-azabicyclo[2.2.1]heptyl-1-carbonitriles 10a-e were sequentially derivatised according to the methodology of scheme 5 below (showing conversion of compound 10a into compounds 16 and 17).

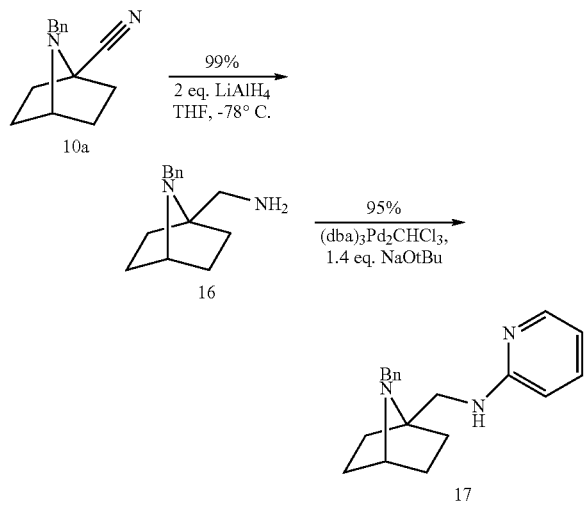

Reduction of compound 10a to 16 by means of $LiAlH_4$ was performed quantitatively. Next, the pyridyl group was introduced onto the side chain of the 7-azabicyclo[2.2.1]hept-1-yl ring by means of a Pd catalysed cross-coupling reaction. Standard Buchwald conditions were used to test different ligands: Binap, dppp and di-Cert-butyl-{1-[2-(dicyclohexylphosphanyl)ferrocenyl]ethyl}phosphine (dfep) provided conversions of 48%, 12% and 10% respectively. Using the more efficient ligand Binap, several pyridyl groups and operating conditions were tested, as shown in table 1 indicating the resulting yields. The best results were obtained using 1 eq. 2-bromopyridine, 1.4 eq. sodium Pert-butoxide and 4 mole % of a $(dba)_3Pd_2CHCl_3$ catalyst.

TABLE 1

|  | 2-chloro-pyridine | 2-bromopyridine | | |
|---|---|---|---|---|
|  | 1.2 equiv. amine | 1.2 equiv. amine | 1 equiv. amine | 0.8 equiv. amine |
| 2% catalyst | 56% | 59% | 91% | 85% |
| 4% catalyst | 62% | 77% | 95% | N/A[a] |

[a]N/A: not available

Ligand requirements for this reaction proved to be highly dependent upon the substrate. Using 2-bromopyridine the ligand of choice was Binap, giving a conversion of 95% over 2 days. Using 3-bromopyridine and dfep as a ligand, a 55% conversion was obtained and the secondary amine 18 (shown in scheme 6 below) was isolated in 47% yield after column chromatography.

Details of these syntheses are as follows:

Synthesis of Compound 16

In a dry 50 ml flask 0.72 g $LiAlH_4$ (18.8 mmole) was suspended in 10 ml dry THF. The flask was placed under inert $N_2$-atmosphere and cooled to −78° C. To this suspension 2 g 7-benzyl-7-azabicyclo[2.2.1]heptyl-1-carbonitrile 10a (9.4 mmole) dissolved in 30 ml dry THF was added dropwise. The cooling equipment was removed and the reaction mixture was allowed to heat up to room temperature. The reaction mixture was stirred overnight. After cooling to 0° C., water was carefully added to neutralise the excess $LiAlH_4$. The reaction mixture was dried by adding $MgSO_4$ and, after filtration of the solids and removal of the volatile components, 7-benzyl-7-azabicyclo[2.2.1]hept-1-yl)-methylamine 16 was obtained (yield 99%) as a slightly yellow solid and was characterised by proton ($^1$H-NMR) and carbon ($^{13}$C-NMR) nuclear magnetic resonance, mass spectrum ($MS^{ES}$), infrared (IR) spectrophotometry and melting point as follows:

$^1$H-NMR (300 MHz, $CDCl_3$) (ppm): 1.31-1.43 (4H, m, $2×CH_aH_bCH$, $2×CH_aH_bC_q$); 1.50-1.60 (2H, br. s, $NH_2$); 1.65-1.87 (4H, m, $2×CH_aH_bCH$, $2×CH_aH_bC_q$); 2.90 (2H, s, $CH_2NH_2$); 3.18 (1H, t, J=4.4 Hz, $CH_2CHCH_2$); 3.42 (2H, s, $NCH_2Ph$) and 7.19-7.42 (5H, m, 5×CH, Ph.);

$^{13}$C-NMR (75 MHz, $CDCl_3$) (ppm): 28.29 (2×$CH_2CH$); 31.35 (2×$CH_2C_q$); 43.51 ($CH_2NH_2$); 49.11 ($NCH_2Ph$); 59.77 ($CH_2CHCH_2$); 69.36 ($CH_2C_qCH_2$); 126.80 (CH, Ph.); 128.28 (2×CH, Ph.); 128.72 (2×CH, Ph.) and 140.35 ($C_q$, Ph.);

IR ($cm^{-1}$): 3368 ($NH_2$);
$MS^{ES}$ m/z (%): 217 (M+H$^+$, 100); and
Melting point 71-72.7° C.

Synthesis of Compound 17

In a dry tube 0.66 g (3 mmole) 7-benzyl-7-azabicyclo[2.2.1]hept-1-yl)-methylamine 16, 0.47 g (3 mmole) 2-bromopyridine and 0.41 g (4.2 mmole) sodium tert-butoxide were dissolved in 25 ml dry toluene. The tube was flushed with argon and 124 mg (0.12 mmole, 8 mole % Pd) of a catalyst $(dba)_3Pd_2CHCl_3$ and 149 mg (0.24 mmole, 8 mole %) Binap were added. The tube was flushed a second time with argon, closed and heated to 70° C. Fifty hours later the reaction was ended by filtration of the Pd-catalyst. Toluene was removed under vacuum and the residue was re-dissolved in dichloromethane. A saturated $NaHCO_3$ solution was added and extracted twice with dichloromethane. The combined organic phases were dried over $MgSO_4$ and evaporated. Compound 15 was obtained as a orange oil in 95% yield and was characterised by proton ($^1$H-NMR) and carbon ($^{13}$C-NMR) nuclear magnetic resonance, mass spectrum ($MS^{ES}$) and infrared (IR) spectrophotometry as follows:

$^1$H-NMR (300 MHz, $CDCl_3$) (ppm): 1.30-1.47 (4H, m, $2×CH_aH_bCH$, $2×CH_aH_bC_q$); 1.72-1.89 (4H, m, $2×CH_aH_bCH$, $2×CH_aH_bC_q$); 3.19 (1H, br s, $CH_2CHCH_2$); 3.40 (2H, s, $NCH_2Ph$); 3.49 (2H, d, J=4.4 Hz, $C_qCH_2NH$); 4.89 (1H, ~t, J=4.4 Hz, NH); 6.30 (1H, d, J=8.3 Hz, $C_qCH$ pyr.); 6.49 (1H, dxdxd, $J_1$=7.0 Hz, $J_2$=5.0 Hz, $J_3$=0.8 Hz, NCHCH pyr.); 7.16-7.38 (6H, m, 5×CH Ph, $C_q$CHCH pyr.) and 8.06 (1H, m, NCH pyr.);

$^{13}$C-NMR (75 MHz, $CDCl_3$) (ppm): 28.44 (2×$CH_2$ ring); 32.03 (2×$CH_2$ ring); 43.02 ($CH_2NH$); 48.84 ($NCH_2Ph$); 59.54 ($CH_2CHCH_2$); 67.54 ($CH_2C_qCH_2$); 107.48 ($C_qCH$ pyr.); 112.52 (NCHCH pyr.); 126.89 (CH Ph.); 128.35 (2×CH Ph.); 128.72 (2×CH Ph.); 137.19 ($C_q$CHCH pyr.); 140.35 ($C_q$ Ph.); 148.09 (NCH pyr.) and 158.93 ($C_q$ pyr.);

IR ($cm^{-1}$): 3375 (NH); and
$MS^{ES}$ m/z (%): 294 (M+H$^+$, 100).

Synthesis of Compound 18

Synthesis proceeded by analogy to compound 17, except that t-butyl-{1-[2-(dicyclohexylphosphanyl)ferrocenyl]ethyl}phosphine (dfep) was used as a ligand and 3-bromopyridine used instead of 2-bromopyridine. Purification was performed by means of column chromatography. Compound (yield 47%) was characterised by proton ($^1$H-NMR) and carbon ($^{13}$C-NMR) nuclear magnetic resonance, mass spectrum ($MS^{ES}$), infrared (IR) spectrophotometry and melting point as follows:

$^1$H-NMR (300 MHz, $CDCl_3$) (ppm): 1.36-1.50 (4H, m, $2×CH_{exo}H_{endo}CH$, $2×CH_aH_bC_q$); 1.79-1.90 (4H, m, $2×CH_{exo}H_{endo}CH$, $2×CH_aH_bC_q$); 3.21-3.27 (3H, m, $CH_2CHCH_2$, $CH_2NH$); 3.38 (2H, s, $NCH_2Ph$); 4.17 (1H, ~t, J=4.1 Hz, NH); 6.76 (1H, dxdxd, $J_1$=8.3 Hz, $J_2$=2.8 Hz, $J_3$=1.1 Hz, $C_q$CHCH pyr.); 7.02 (1H, dxd, $J_1$=8.3 Hz, $J_2$=4.7 Hz, $C_q$CHCH pyr.); 7.15-7.37 (5H, m, 5×CH Ph); 7.90 (1H, dxd, $J_1$=4.7 Hz, $J_2$=1.1 Hz, NCHCH pyr.) and 7.93 (1H, d, J=2.8 Hz, $NCHC_q$ pyr.);

$^{13}$C-NMR (75 MHz, $CDCl_3$) (ppm): 28.48 (2×$CH_2$ ring); 32.07 (2×$CH_2$ ring); 44.62 ($CH_2NH$); 48.94 ($NCH_2Ph$); 60.09 ($CH_2CHCH_2$); 67.65 ($CH_2C_qCH_2$); 77.13 ($CDCl_3$); 118.25 ($C_q$CHCH pyr.); 123.67 ($C_q$CHCH pyr.); 127.00 (CH Ph.); 128.43 (2×CH Ph.); 128.58 (2×CH Ph.); 135.71 (NCHC$_q$ pyr.); 138.37 (NCHCH pyr.); 140.19 ($C_q$ Ph.) and 144.61 ($C_q$ pyr.);

IR ($cm^{-1}$): 3372 (NH);
$MS^{ES}$ m/z (%): 294 (M+H$^+$, 100); and
Melting point 66.8-68.6° C.

EXAMPLE 6

Preparation of 7-azabicyclo[2.2.1]hept-1-ylmethyl)-pyridinyl-amines

Removal of the protective benzyl group of compounds 17 and 18 was performed by refluxing them in methanol, and using ammonium formate as reducing agent, as shown in scheme 6 below. Compound 5 was obtained after 1 hour of reflux, while for compound 19 a period of 2 hours was necessary to drive the reaction to completion. The low yield for compound 19 may be attributed to a troublesome purification. Compound 5 was easily separated from the excess ammonium formate by dissolution in dry diethyl ether. Compound 19 however does not dissolve in diethyl ether. Eventually, separation of the non-reacted ammonium formate was obtained by a temperature controlled selective crystallisation from hexane.

Scheme 6

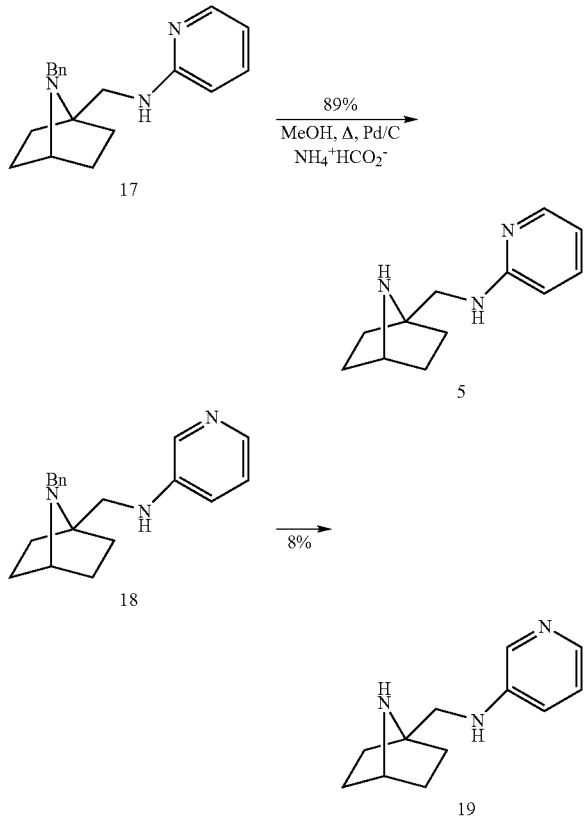

Details of these syntheses are as follows:

Synthesis of Compound 5

In a 50 ml flask 0.76 g (2.3 mmole) 7-benzyl-7-azabicyclo[2.2.1]hept-1-ylmethyl)-pyridin-2-yl-amine 17 and 0.67 g (10.6 mmole) ammonium formate were dissolved in 40 ml methanol. To this solution 0.38 g of a Pd/C catalyst (5% Pd) was added. The suspension was refluxed during one hour, after which the Pd/C catalyst was filtered off and the methanol evaporated. Compound 5 (yield 89%) was extracted from the remaining solids by means of dry diethyl ether and was characterised by proton ($^1$H-NMR) and carbon ($^{13}$C-NMR) nuclear magnetic resonance, mass spectrum ($MS^{ES}$), infrared (IR) spectrophotometry and melting point as follows:

$^1$H-NMR (300 MHz, CDCl$_3$) (ppm): 1.42-1.62 (6H, m, 4×CH$_{exo}$H$_{endo}$ ring, 2×C$_q$CH$_{exo}$H$_{endo}$ ring); 1.66-1.80 (2H, m, 2×CHCH$_{exo}$H$_{endo}$); 1.86-1.97 (1H, br. s, CHNH); 3.64 (1H, t, J=4.5 Hz, CH$_2$CHCH$_2$); 3.66 (2H, d, J=5.8 Hz, NCH$_2$); 4.84-4.95 (1H, m, CH$_2$NH); 6.46 (1H, dxt, J$_1$=8.4 Hz, J$_2$=0.8 Hz, C$_q$CHCH pyr.); 6.55 (1H, dxdxd, J$_1$=7.0 Hz, J$_2$=5.0 Hz, J$_3$=0.8 Hz, NCHCH pyr.); 7.39 (1H, dxdxd, J$_1$=8.4 Hz, J$_2$=7.0 Hz, J$_3$=1.9 Hz, C$_q$CHCH pyr.) and 8.07 (1H, dxdxd, J$_1$=5.0 Hz, J$_2$=1.9 Hz, J$_3$=0.8 Hz, NCHCH pyr.);

$^{13}$C-NMR (75 MHz, CDCl$_3$) (ppm): 31.75 (2×CHCH$_2$ ring); 32.94 (2×C$_q$CH$_2$ ring); 45.46 (CH$_2$NH); 57.07 (CH$_2$CHCH$_2$); 67.30 (CH$_2$C$_q$CH$_2$); 77.13 (CDCl$_3$); 107.45 (C$_q$CHCH pyr.); 112.78 (NCHCH pyr.); 137.39 (C$_q$CHCH pyr.); 148.08 (NCHCH pyr.) and 159.12 (C$_q$ pyr.);

IR (cm$^{-1}$): 3410 (NH) and 3263 (NH);

$MS^{ES}$ m/z (%): 204 (M+H$^+$, 100); and melting point: 73.8-74.2° C.

Synthesis of Compound 19

0.18 g (0.61 mmole) 7-benzyl-7-azabicyclo[2.2.1]hept-1-ylmethyl)pyridin-3-ylamine 18 and 0.15 g (2.45 mmole) ammonium formate were dissolved in 20 ml methanol. To this solution 0.09 g of a Pd/C catalyst (5% Pd) was added. The suspension was refluxed during 2 hours after which the Pd/C catalyst was removed by filtration and methanol was evaporated. The solid residue was treated with boiling hexane, decanted and cooled to −20° C. Crystals of compound 19 (formed in 8% yield) were characterised by proton ($^1$H-NMR) and carbon ($^{13}$C-NMR) nuclear magnetic resonance, mass spectrum ($MS^{ES}$) and infrared (IR) spectrophotometry as follows:

$^1$H-NMR (300 MHz, CDCl$_3$) (ppm): 1.45-1.68 (6H, m, 2×CHCH$_{exo}$H$_{endo}$, 2×C$_q$CH$_2$); 1.73-1.96 (3H, m, 2×CHC H$_{exo}$H$_{endo}$, CHNH); 3.44 (2H, d, J=4.1 Hz, CH$_2$NH); 3.68 (1H, t, J=4.5 Hz, CH$_2$CHCH$_2$); 4.30 (1H, br. s, CH$_2$NH); 6.92 (1H, dxdxd, J$_1$=8.3 Hz, J$_2$=2.7 Hz, J$_3$=1.1 Hz, C$_q$CHCH pyr.); 7.07 (1H, dxd, J$_1$=8.3 Hz, J$_2$=4.7 Hz, C$_q$CHCH pyr.); 7.94 (1H, dxd, J$_1$=1.1 Hz, J$_2$=4.7 Hz, NCHCH pyr.) and 8.06 (1H, d, J=2.7 Hz, NCHC$_q$ pyr.);

$^{13}$C-NMR (75 MHz, CDCl$_3$) δ (ppm): 31.57 (2×CHCH$_2$); 32.99 (2×C$_q$CH$_2$); 47.02 (CH$_2$NH); 57.20 (CH$_2$CHCH$_2$); 67.40 (CH$_2$C$_q$CH$_2$); 118.47 (C$_q$CHCH pyr.); 123.79 (C$_q$CH CH pyr.); 135.99 (NCHC$_q$ pyr.); 138.70 (NCHCH pyr.) and 144.71 (C$_q$ pyr.);

IR (cm$^{-1}$): 3435 (NH); and $MS^{ES}$ m/z (%): 204.2 (M+H$^+$, 100).

EXAMPLE 7

Synthesis of 7-(4-methoxybenzyl)-7-azabicyclo[2.2.1]heptane-1-carbonitrile

This synthesis was performed according to scheme 2, with details as follows. In a dry, pressure resistant vessel of 20 ml, 1.25 g (6.5 mmole) 4-methanesulfonylcyclohexanone 9, 0.89 g (6.5 mmole) 4-methoxybenzylamine, 1.11 g (13 mmole) acetone cyanohydrine and 1.32 g (13 mmole) triethylamine were dissolved in 16 ml dry methanol. The vessel was closed and heated to 100° C. for 50 hours. Methanol was evaporated and the residue was redissolved in dichloromethane. The solution was washed with a saturated NaHCO$_3$ solution and dried over MgSO$_4$. After filtration of the solids, the volatile components were evaporated. 7-(4-methoxybenzyl)-7-azabicyclo[2.2.1]heptane-1-carbonitrile 6a was obtained as a brown oil in a 97% yield and characterised by proton ($^1$H-NMR) and carbon ($^{13}$C-NMR) nuclear magnetic resonance, and mass spectrum ($MS^{ES}$) as follows:

$^1$H-NMR (300 MHz; CDCl$_3$; Me$_4$Si) (ppm): 1.35-1.44 (2H, m, 2×CH$_a$H$_b$CH), 1.77-1.88 (4H, m, 2×CH$_a$H$_b$CH, 2×C H$_a$H$_b$C$_q$), 2.09-2.17 (2H, m, 2×CH$_a$H$_b$C$_q$), 3.26 (1H, t, CH$_2$C HCH$_2$), 3.58 (2H, s, NCH$_2$Ph), 3.81 (3H, s, OCH$_3$), 6.87 (2H, d, 2×OCqCHCH) and 7.28 (2H, d, 2×OCqCHCH);

$^{13}$C-NMR (75 MHz; CDCl$_3$; Me$_4$Si) (ppm): 28.0 (2× CH$_2$CH), 34.39 (2×CH$_2$C$_q$), 49.94 (NCH$_2$Ph), 55.41 (OCH$_3$), 58.34 (CH$_2$CHCH$_2$), 59.51 (N—C$_q$), 113.83 (OC$_q$ CH), 120.51 (C≡N), 129.92 (OC$_q$CHCH), 130.87 (NCH$_2$ C$_q$) and 158.91 (OC$_q$); and $MS^{ES}$ m/z (%) 243 (M+H$^+$, 100%), 91 (15).

EXAMPLE 8

Synthesis of 7-(4-methoxybenzyl)-7-azabicyclo[2.2.1]hept-1-yl)-(6-chloro-pyridin-3-yl)-methanone In a dry 50 ml flask 2.47 g (10.3 mmole) 2-chloro-5-iodopyridine was dissolved in 20 ml of dry diethyl ether. The flask was placed under $N_2$-atmosphere, cooled to $-78°$ C. and 5.1 ml of a 2M solution (10.3 mmole) butyl lithium (BuLi) was added. The reaction mixture was stirred for one hour at $-78°$ C. before adding 1 g (4.1 mmole) of the nitrile compound of example 7. Stirring was continued for 30 minutes at $-78°$ C. and the reaction mixture was then allowed to slowly warm up to room temperature. After 16 hours at room temperature methanol was added in order to neutralise the excess BuLi, and the volatile components were evaporated. The reaction mixture was redissolved in 25 ml of a 1:1 mixture of methanol and 0.5M HCl. 0.5 g of silica gel was added and the mixture was stirred for 15 hours at room temperature. The pH was adjusted to approximately 8 by adding a concentrated $NaHCO_3$ solution. The resulting reaction product was extracted three times by means of dichloromethane and the combined organic phases were dried over $MgSO_4$. After filtration of the solids and evaporation of the volatile components, purification was performed by means of column chromatography, and any remaining 2-chloropyridine was removed by sublimation under high vacuum conditions. 7-(4-methoxybenzyl)-7-azabicyclo[2.2.1]hept-1-yl)-(6-chloro-pyridin-3-yl)-methanone was obtained in a 62% yield and characterised by proton ($^1$H-NMR) and carbon ($^{13}$C-NMR) nuclear magnetic resonance, infrared (IR) spectrophotometry and mass spectrum ($MS^{ES}$) as follows:

IRcm$^{-1}$) 1672 (C=O);
$^1$H-NMR (300 MHz; CDCl$_3$; Me$_4$Si) (ppm): 1.42-1.50 (2H, m, 2×CHCH$_{exo}$H$_{endo}$), 1.74 (2H, br. s, 2×C$_q$CH$_a$CH$_b$), 1.97 (2H, br. s, 2× CHCH$_{exo}$H$_{endo}$), 2.29 (2H, br. s, 2×C$_q$CH$_a$CH$_b$), 3.33 (2H, s, NCH$_2$), 3.42 (1H, t, CH$_2$CHCH$_2$), 3.75 (3H, s, OCH$_3$), 6.77 (2H, d, 2×OC$_q$CHCH), 7.14 (2H, d, 2×OC$_q$CHCH), 7.38 (1H, d, ClC$_q$CH), 8.68 (1H, dxd, ClC$_q$CHCH pyr.) and 9.69 (1H, d, CHN pyr.);
$^{13}$C-NMR (75 MHz; CDCl$_3$; Me$_4$Si) (ppm): 28.0-32.0 (2× CH$_2$CHN), 36.0-38.0 (2×CH$_2$C$_q$N), 49.7 (NCH$_2$), 55.2 (OCH$_3$), 59.9 (CH$_2$CHCH$_2$), 77.39 (CH$_2$C$_q$CH$_2$), 113.70 (2×OC$_q$CH Ph.), 124.1 (ClC$_q$CH), 129.5 (C$_q$ pyr.), 129.9 (2×OC$_q$CHCH Ph.), 130.9 (C$_q$ pyr.), 139.9 (ClC$_q$CHCH), 152.9 (C$_q$CHN pyr.), 155.2 (OC$_q$CHCHC$_q$), 158.8 (OC$_q$CHCHC$_q$) and 199.2 (C$_q$=O); and
$MS^{ES}$ m/z (%) 375 (M+H3O$^+$, 5%), 359 (M+H$^+$, 35), 357 (M+H$^+$, 100).

EXAMPLE 9

Synthesis of 7-aza-bicyclo[2.2.1]hept-1-yl)-(6-chloro-pyridin-3-yl)-methanone

In a 50 ml flask 0.58 g (1.6 mmole) of the compound of example 8 was dissolved in 30 ml of a 1/3 water/acetonitrile mixture. The flask was cooled to 0° C. and 17.4 g (1.3 mole) cerium ammonium nitrate was added. After 1 hour at 0° C. and 16 hours at room temperature, acetonitrile was evaporated. Water (20 ml) was added and acidified to pH 1 using 3M HCl. The mixture was washed with diethylether and the pH is adjusted to 9 using NaHCO$_3$. After extraction with CH$_2$Cl$_2$, the crude reaction product was purified by means of column chromatography. 7-azabicyclo[2.2.1]hept-1-yl)-(6-chloro-pyridin-3-yl)-methanone was thus obtained in a 46% yield and characterised by proton (1H-NMR) and carbon ($^{13}$C-NMR) nuclear magnetic resonance, infrared (IR) spectrophotometry and mass spectrum ($MS^{ES}$) as follows:

IR (cm$^{-1}$): 2956 (NH) and 1678 (C=O);
$^1$H-NMR (300 MHz; CDCl$_3$; Me$_4$Si) (ppm): 1.73-1.82 (2H, CH$_2$ ring), 2.04-2.17 (6H, CH$_2$ ring including 2×CH$_{endo}$H$_{exo}$), 4.12 (1H, s, CH ring), 7.44 (1H, d, CHC$_q$Cl pyr.), 8.40 (1H, dxd, CHCHC$_q$Cl pyr.) and 9.11 (1H, d, NCH pyr.);
$^{13}$C-NMR (75 MHz; CDCl$_3$; Me$_4$Si) (ppm): 30.3 (2× CH$_2$CHCH$_2$ or CH$_2$C$_q$CH$_2$), 33.8 (2×CH$_2$CHCH$_2$ or CH$_2$C$_q$CH$_2$), 53.5 (CH$_2$C$_q$CH$_2$), 57.1 (CH$_2$CHCH$_2$), 124.6 (CH pyr.), 129.7 (C$_q$CHCHCCl), 139.7 (CH pyr.), 151.0 (CH pyr.), 155.9 (C$_q$Cl); and
$MS^{ES}$ m/z (%): 239 (M+H$^+$, 35), 237 (M+H$^+$, 100).

EXAMPLE 10

Synthesis of 7-(4-methoxybenzyl)-7-aza-bicyclo[2.2.1]hept-1-yl)-pyridin-3-yl-methanone Synthesis was performed according to scheme 4 and under the same conditions as example 4, but starting from the nitrile compound of example 7. 7-(4-methoxybenzyl)-7-aza-bicyclo[2.2.1]hept-1-yl)-pyridin-3-yl-methanone was obtained in a 48% yield and characterised by proton ($^1$H-NMR) and carbon ($^{13}$C-NMR) nuclear magnetic resonance, infrared (IR) spectrophotometry and mass spectrum ($MS^{ES}$) as follows:

IR (cm$^{-1}$): 1667 (C=O);
$^1$H-NMR (300 MHz; CDCl$_3$; Me$_4$Si) (ppm): 1.47 (2H, dxdxd, 2×CHCH$_{exo}$H$_{endo}$), 1.75 (2H, br. s, 2×C$_q$CH$_a$H$_b$), 1.91-2.07 (2H, m, 2×CHCH$_{exo}$H$_{endo}$), 2.26-2.40 (2H, m, 2×C$_q$CH$_a$H$_b$), 3.33 (2H, s, NCH$_2$Ph), 3.41 (1H, t, CH$_2$CHCH$_2$), 3.77 (3H, s, OCH$_3$), 6.80 (2H, d, 2×MeOC$_q$CH), 7.17 (2H, d, MeOC$_q$CHCH), 7.40 (1H, dxd, NCHCH pyr.), 8.76 (2H, m, NCHCH pyr.+C$_q$CHCH pyr.) and 9.89 (1H, br.s, C$_q$CHN pyr.);
$^{13}$C-NMR (75 MHz; CDCl$_3$; Me$_4$Si) (ppm): 30.3-34.5 (4× CH$_2$), 49.59 (NCH$_2$Ph), 55.30 (OCH$_3$), 59.60 (CH$_2$CHCH$_2$), 77.16 (CDCl$_3$), 77.57 (CH$_2$C$_q$CH$_2$), 113.72 (2×OC$_q$CH), 123.41 (NCHCH pyr.), 129.80 (C$_q$ pyr.), 130.67 (2×OC$_q$CHCH), 131.33 (C$_q$Ph.), 137.23 (C$_q$CHCH pyr.), 151.88 (C$_q$CHN pyr.), 153.32 (NCHCH pyr.), 158.71 (MeOC$_q$), 200.51 (CO); and
$MS^{ES}$ m/z (%) 323 (M+H$^+$, 100).

EXAMPLE 11

Synthesis of 7-azabicyclo[2.2.1]hept-1-yl)-pyridin-3-yl-methanone

In a 60 ml flask 1.29 g (4.0 mmole) of the compound of example 10 was dissolved in 60 ml of a 1/3 water/acetonitrile mixture. The flask was cooled to 0° C. and 43.87 g (1.32 mole) cerium ammonium nitrate was added. After 1 hour at 0° C. and 16 hours at room temperature, acetonitrile was evaporated. Water was added (20 ml) and acidified to pH 1 using 3M HCl. The mixture was washed with diethylether and the pH is adjusted to 9 using NaHCO$_3$. After extraction with CH$_2$Cl$_2$, the crude product was purified by means of column chromatography. 7-azabicyclo[2.2.1]hept-1-yl)-pyridin-3-yl-methanone was obtained in a 53% yield and characterised by proton ($^1$H-NMR) and carbon ($^{13}$C-NMR) nuclear magnetic resonance, infrared (IR) spectrophotometry and mass spectrum ($MS^{ES}$) as follows:

IR (cm$^{-1}$) 3191 (NH), 1676 (C=O);

$^1$H-NMR (300 MHz; CDCl$_3$; Me$_4$Si) (ppm): 1.58-1.67 (2H, m, 2×NC$_q$CH$_a$CH$_b$), 1.82-1.95 (6H, m, C$_q$CH$_a$CH$_b$, 2×CHCH$_{exo}$H$_{endo}$, 2×CHCH$_{exo}$H$_{endo}$), 3.81 (1H, t, NCH), 7.38 (1H, dxd, NCHCH pyr.), 8.48 (1H, dxd, NCHCHCH pyr.), 8.73 (1H, dxt, NCHCH pyr.) and 9.40 (1H, d, NCHC$_q$ pyr.);

$^{13}$C-NMR (75 MHz; CDCl$_3$; Me$_4$Si) (ppm): 31.4 (2×CH$_2$C$_q$N), 35.0 (2×CCH$_2$CHN), 57.0 (CH$_2$CHCH$_2$), 75.3 (NC$_q$), 123.4 (NCHCHCH pyr.), 131.8 (C$_q$ pyr.), 136.9 (NCHCHCH pyr.), 150.9 (NCHC$_q$ pyr.), 153.1 (NCHCHCH pyr.) and 201.2 (C=O); and MS$^{ES}$ m/z (%): 203 (M+H$^+$, 100%).

EXAMPLE 12

Synthesis of 7-(pyridin-3-ylmethyl)-7-aza-bicyclo [2.2.1]heptane-1-carbonitrile

In a dry pressure resistant vessel of 20 ml, 1.0 g (5.20 mmole) 4-methanesulphonylcyclohexanone, 0.56 g (5.20 mmole) 3-picolylamine, 0.89 g (10.4 mmole) acetonecyanohydrin and 1.06 g (10.4 mmole) triethylamine were dissolved in 16 ml dry methanol. The vessel was then closed and heated for 50 hours at 100° C. Methanol was then evaporated and the residue was redissolved in dichloromethane, washed with a saturated NaHCO$_3$ solution, dried over MgSO$_4$, filtered and evaporated. The residue was further purified by means of column chromatography. 7-(pyridin-3-ylmethyl)-7-aza-bicyclo[2.2.1]heptane-1-carbonitrile (structural formula below) was thus obtained in a 50% yield and characterised by proton ($^1$H-NMR) and carbon ($^{13}$C-NMR) nuclear magnetic resonance, infrared (IR) spectrophotometry and mass spectrum (MS$^{ES}$) as follows:

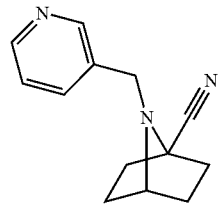 [SMILES: N#CC12CCC(CC1)N2Cc1cccnc1]

IR (cm$^{-1}$): 2242 (C≡N);
$^1$H-NMR (300 MHz, CDCl$_3$) (ppm): 1.39-1.48 (2H, m, 2×CH$_a$H$_b$C$_q$); 1.79-1.93 (4H, m, 2×CH$_a$H$_b$C$_q$, 2×CHCH$_{exo}$H$_{endo}$); 2.12-2.21 (2H, m, 2×CHCH$_{exo}$H$_{endo}$); 3.24 (1H, t); 3.67 (2H, s, NCH$_2$); 7.28 (1H, dxd, NCHCH pyr.); 7.76 (1H, d, NCHC$_q$CH pyr.), 8.52 (1H, d, NCHCH pyr.) and 8.58 (1H, s, NCHC$_q$ pyr.);
$^{13}$C-NMR (75 MHZ, CDCl$_3$) δ (ppm): 28.0 (2×CH$_2$C$_q$ ring); 34.3 (2×CH$_2$CH ring); 47.8 (NCH$_2$C$_q$); 58.7 (CH$_2$CHCH$_2$ ring); 59.6 (CH$_2$NC$_q$ ring); 120.2 (C≡N); 123.5 (NCHCH pyr.); 134.3 (C$_q$ pyr.); 136.4 (NCHC$_q$CH pyr.); 148.8 (NCCHCH pyr.) and 149.9 (NCCHC$_q$ pyr.); and
MS$^{ES}$ m/z (%): 214.2 (M+H$^+$, 100).

Example 13

Synthesis of 7-(pyridin-2-ylmethyl)-7-aza-bicyclo [2.2.1]heptane-1-carbonitrile

In a dry pressure resistant vessel of 20 ml, 1.0 g (5.20 mmole) 4-methanesulphonylcyclohexanone, 0.56 g (5.20 mmole) 2-picolylamine, 0.89 g (10.4 mmole) acetone cyanhydrin and 1.06 g (10.4 mmole) triethylamine were dissolved in 16 ml dry methanol. The vessel was closed and heated for 50 hours at 100° C. Methanol was evaporated and the residue was re-dissolved in dichloromethane, washed with a saturated NaHCO$_3$ solution, dried over MgSO$_4$, filtered and evaporated. The residue was further purified by means of column chromatography. 7-(pyridin-3-ylmethyl)-7-aza-bicyclo[2.2.1]heptane-1-carbonitrile (structural formula below) was thus obtained in a 69% yield and characterised by proton ($^1$H-NMR) and carbon ($^{13}$C-NMR) nuclear magnetic resonance, infrared (IR) spectrophotometry and mass spectrum (MS$^{ES}$) as follows.

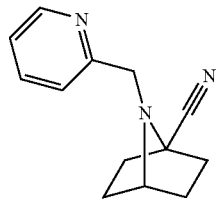 [SMILES: N#CC12CCC(CC1)N2Cc1ccccn1]

IR (cm$^{-1}$): 2242 (C≡N);
$^1$H-NMR (300 MHz, CDCl$_3$) δ (ppm): 1.40-1.49 (2H, m, 2×CHCH$_{exo}$H$_{endo}$); 1.82-2.01 (4H, m, 2×CH$_a$H$_b$C$_q$N, 2×CHCH$_{exo}$H$_{endo}$); 2.13-2.23 (2H, m, CH$_a$H$_b$C$_q$N); 3.38 (1H, t, NCH); 3.83 (2H, s, NCH$_2$); 7.19 (1H, dxd, NCHCH pyr.); 7.55 (1H, d, C$_q$CH pyr.), 7.69 (1H, txd, C$_q$CHCH pyr.) and 8.38 (1H, dxd, NCH pyr.);
$^{13}$C-NMR (75 MHZ, CDCl$_3$) δ (ppm): 28.1 (2×CH$_2$C$_q$ ring); 34.4 (CH$_2$CHCH$_2$); 52.5 (NCH$_2$C$_q$); 59.5 (CH$_2$CHCH$_2$); 59.8 (CH$_2$C$_q$CH$_2$); 120.2 (C≡N); 122.3 (NCHCH pyr.); 123.0 (C$_q$CH pyr.); 136.7 (C$_q$CHCH pyr.); 149.1 (NCH pyr.) and 158.9 (NC$_q$ pyr.); and
MS$^{ES}$ m/z (%): 214.2 (M+H$^+$, 100).

EXAMPLE 14

Competitive Enzyme Binding Assays of Compounds Wherein R$_0$ is Hydrogen

Two illustrative compounds of this invention (compound 15 of example 4, referred as EPB001 in table 2 below, and compound 5 of example 6, referred as EPB002 in table 2 below) have each been tested in a series of 18 binding assays for various enzymes, including adrenergic receptors, human cannabinoid receptors, human dopamine receptors, central benzodiazepine receptor, GABA receptor, glycine receptor, muscarinic receptors, neuronal nicotinic receptors, muscular nicotinic receptors, and serotonine receptor. Details of each binding assay procedure are given below.
Non-selective α$_1$-Adrenergic Receptor (Antagonist Radioligand):
The purpose is to evaluate the affinity of compounds for the non-selective α$_1$-adrenergic receptor in the rat cerebral cortex determined in a radioligand is binding assay according to Greengrass et al. in *Eur. J. Pharmacol.* (1979) 55: 323. The experimental protocol is as follows. Membrane homogenates of cerebral cortex (160 μg protein) are incubated for 60 minutes at 22° C. with 0.25 nM [$^3$H]prazosin in the absence or presence of the test compound in a buffer containing 50 mM Tris-HCl (pH 7.4), 150 mM NaCl, 5 mM EDTA and 0.1% BSA. Non-specific binding is determined in the presence of 0.5 μM prazosin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is prazosin, which is tested in each experiment at several concentrations to obtain a competition curve from which its $IC_{50}$ is calculated.

Non-selective Adrenergic $\alpha_2$ Receptor (Antagonist Radioligand):

The purpose is to evaluate the affinity of compounds for the non-selective $_2$-adrenergic receptor in the rat cerebral cortex determined in a radioligand binding assay according to Uhlen et al. in *Pharmacol. Toxicol.* (1991) 69:341. The experimental protocol is as follows. Membrane homogenates of cerebral cortex (160 μg protein) are incubated for 60 minutes at 22° C. with 0.5 nM [$^3$H]RX 821002 in the absence or presence of the test compound in a buffer containing 50 mM Tris-HCl (pH 7.4), 2 mM $MgCl_2$ and 1 mM EDTA. Non-specific binding is determined in the presence of 100 μM(-)epinephrine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is yohimbine, which is tested in each experiment at several concentrations to obtain a competition curve from which its $IC_{50}$ is calculated.

Human Adrenergic $\beta_1$ Receptor (Agonist Radioligand):

The purpose is to evaluate the affinity of compounds for the agonist site of the human $\beta_1$-adrenergic receptor in transfected HEK-293 cells determined in a radioligand binding assay according to Levin et al. in *J. Biol. Chem.* (2002) 277: 30429. The experimental protocol is as follows. Cell membrane homogenates (5 μg protein) are incubated for 60 minutes at 22° C. with 0.15 nM [$^3$H]CGP 12177 in the absence or presence of the test compound in a buffer containing 50 mM Tris-HCl (pH 7.4), 10 mM $MgCl_2$, 2 mM EDTA and 0.1% BSA. Nonspecific binding is determined in the presence of 50 μM alprenolol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is atenolol, which is tested in each experiment at several concentrations to obtain a competition curve from which its $IC_{50}$ is calculated.

Human Adrenergic $\beta_2$ Receptor (Agonist Radioligand)

The purpose is to evaluate the affinity of compounds for the agonist site of the human $\beta_2$-adrenergic receptor in transfected CHO cells determined in a radioligand binding assay according to Joseph et al. in *Naunyn-Schmiedeberg's Arch. Pharmacol.* (2004) 369:525. The experimental protocol is as follows. Cell membrane homogenates (32 μg protein) are incubated for 120 minutes at 22° C. with 0.3 nM [$^3$H]CGP 12177 in the absence or presence of the test compound in a buffer containing 10 mM $NaH_2PO_4/Na_2HPO_4$ (pH 7.4), 85 mM NaCl, 30 mM KCl, 1 mM $MgCl_2$, 5.5 mM glucose, 0.005% bacitracin and 0.1% BSA. Nonspecific binding is determined in the presence of 50 μM alprenolol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is ICI 118551, which is tested in each experiment at several concentrations to obtain a competition curve from which its $IC_{50}$ is calculated.

Central Benzodiazepine Receptor (Agonist Radioligand)

The purpose is to evaluate the affinity of compounds for the agonist site of the central benzodiazepine receptor in the rat cerebral cortex determined in a radioligand binding assay according to Speth et al in *Life Sci.* (1979) 24:351. The experimental protocol is as follows. Membrane homogenates of cerebral cortex (80 μg protein) are incubated for 60 minutes at 4° C. with 0.4 nM [$^3$H]flunitrazepam in the absence or presence of the test compound in a buffer containing 50 mM Tris-HCl (pH 7.7). Non-specific binding is determined in the presence of 3 μM diazepam. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is diazepam, which is tested in each experiment at several concentrations to obtain a competition curve from which its $IC_{50}$ is calculated.

Human $CB_1$ Cannabinoid Receptor (Agonist Radioligand):

The purpose is to evaluate the affinity of compounds for the agonist site of the human $CB_1$ cannabinoid receptor in transfected CHO cells determined in a radioligand binding assay according to Rinaldi-Carmona in *J. Pharmacol. Exp. Ther.* (1996) 278:871. The experimental protocol is as follows. Cell membrane homogenates (20 μg protein) are incubated for 120 minutes at 37° C. with 0.5 nM [$^3$H]CP 55940 in the absence or presence of the test compound in a buffer containing 50 mM Tris-HCl (pH 7.4), 5 mM $MgCl_2$, 2.5 mM EDTA and 0.3% BSA. Non-specific binding is determined in the presence of 10 μM WIN 55212-2. Following incubation, the samples are filtered rapidly under vacuum through glass fiber filters (GF/B, Packard) presoaked with 0.3% PEI and rinsed several times with an ice-cold buffer containing 50 mM Tris-HCl (pH 7.4) and 0.5% BSA using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is CP 55940 which is tested in each experiment at several concentrations to obtain a competition curve from which its $IC_{50}$ is calculated.

Human Dopamine $D_1$ Receptor (Antagonist Radioligand):

The purpose is to evaluate the affinity of compounds for the human dopamine $D_1$ receptor in transfected CHO cells determined in a radioligand binding assay according to Zhou et al in *Nature* (1990) 347:76. The experimental protocol is as follows. Cell membrane homogenates (48 μg protein) are incubated for 60 minutes at 22° C. with 0.3 nM [$^3$H]SCH 23390 in the absence or presence of the test compound in a buffer containing 50 mM Tris-HCl (pH 7.4), 5 mM KCl, 5 mM $MgCl_2$, 1.5 mM $CaCl_2$ and 5 mM EDTA. Non-specific binding is determined in the presence of 1 µM SCH 23390. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is SCH 23390, which is tested in each experiment at several concentrations to obtain a competition curve from which its $IC_{50}$ is calculated.

Human Dopamine $D_{2S}$ Receptor (Antagonist Radioligand):

The purpose is to evaluate the affinity of compounds for the human dopamine $D_{2S}$ receptor in transfected HEK-293 cells determined in a radioligand binding assay according to Grandy et al in *Proc. Natl. Acad. Sci. USA* (1989) 86:9762. The experimental protocol is as follows. Cell membrane homogenates (8 µg protein) are incubated for 60 minutes at 22° C. with 0.3 nM [$^3$H]spiperone in the absence or presence of the test compound in a buffer containing 50 mM Tris-HCl (pH 7.4), 120 mM NaCl, 5 mM KCl, 5 mM $MgCl_2$ and 1 mM EDTA. Non-specific binding is determined in the presence of 10 µM (+)butaclamol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is (+)butaclamol, which is tested in each experiment at several concentrations to obtain a competition curve from which its $IC_{50}$ is calculated.

Non-selective GABA Receptor (Agonist Radioligand):

The purpose is to evaluate the affinity of compounds for the agonist site of the non-selective GABA receptor in the rat cerebral cortex determined in a radioligand binding assay according to Tsuji et al in *Antimicrob. Agents Chemother.* (1988) 32:190. The experimental protocol is as follows. Membrane homogenates of cerebral cortex (120 µg protein) are incubated for 60 minutes at 22° C. with 10 nM [$^3$H]GABA in the absence or presence of the test compound in a buffer containing 50 mM Tris-HCl (pH 7.4) and 2.5 mM $CaCl_2$. Non-specific binding is determined in the presence of 100 µM GABA. Following incubation, the samples are filtered rapidly under vacuum through glass fiber filters (GF/B, Packard) and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is GABA, which is tested in each experiment at several concentrations to obtain a competition curve from which its $IC_{50}$ is calculated.

Glycine Receptor (Strychnine Insensitive):

The purpose is to evaluate the affinity of compounds for the strychnine-sensitive glycine receptor in the rat spinal cord, determined in a radioligand binding assay according to Marvizon et al in *Mol. Pharmacol.* (1986) 30:590. The experimental protocol is as follows. Membrane homogenates of spinal cord (250 µg protein) are incubated for 15 min at 0° C. with 2 nM [$^3$H]strychnine in the absence or presence of the test compound in a buffer containing 16.5 mM $NaH_2PO_4$ and 33.5 mM $K_2HPO_4$ (pH 7.1). Nonspecific binding is determined in the presence of 100 µM strychnine. Following incubation, the samples are filtered rapidly under vacuum through glass fiber filters (Filtermat B, Wallac) presoaked with 0.3% PEI and rinsed several times with an ice-cold buffer containing 16.5 mM $NaH_2PO_4$, 33.5 $K_2HPO_4$ and 150 mM NaCl using a 48-sample cell harvester (Mach II, Tomtec). The filters are dried then counted for radioactivity in a scintillation counter (Betaplate 1204, Wallac) using a solid scintillator (Meltilex B/HS, Wallac). The results are expressed as a percent inhibition of the control radioligand specific binding. The standard reference compound is strychnine, which is tested in each experiment at several concentrations to obtain a competition curve from which its $IC_{50}$ is calculated.

Human Muscarinic $M_1$ Receptor (Antagonist Radioligand):

The purpose is to evaluate the affinity of compounds for the human muscarinic $M_1$ receptor in transfected CHO cells determined in a radioligand binding assay according to Dorje et al in *J. Pharmacol. Exp. Ther.* (1991) 256:727. The experimental protocol is as follows. Cell membrane homogenates (45 µg protein) are incubated for 60 minutes at 22° C. with 2 nM [$^3$H]pirenzepine in the absence or presence of the test compound in a buffer containing 50 mM Tris-HCl (pH 7.4), 120 mM NaCl, 5 mM KCl, 5 mM $MgCl_2$ and 1 mM EDTA. Non-specific binding is determined in the presence of 1 µM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is pirenzepine, which is tested in each experiment at several concentrations to obtain a competition curve from which its $IC_{50}$ is calculated.

Human Muscarinic $M_2$ Receptor (Antagonist Radioligand):

The purpose is to evaluate the affinity of compounds for the human muscarinic $M_2$ receptor in transfected CHO cells determined in a radioligand binding assay according to Dorje et al in *J. Pharmacol. Exp. Ther.* (1991) 256:727. The experimental protocol is as follows. Cell membrane homogenates (60 µg protein) are incubated for 60 minutes at 22° C. with 2 nM [$^3$H]AF-DX 384 in the absence or presence of the test compound in a buffer containing 50 mM Tris-HCl (pH 7.4), 120 mM NaCl, 5 mM KCl, 5 mM $MgCl_2$ and 1 mM EDTA. Non-specific binding is determined in the presence of 1 µM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is methoctramine, which is tested in each experiment at several concentrations to obtain a competition curve from which its $IC_{50}$ is calculated.

Human Muscarinic $M_3$ Receptor (Antagonist Radioligand):

The purpose is to evaluate the affinity of compounds for the human muscarinic $M_2$ receptor in transfected CHO cells determined in a radioligand binding assay according to Peralta et al in *EMBO. J.* (1987) δ: 3923 The experimental protocol is as follows. Cell membrane homogenates (8 µg protein) are incubated for 60 minutes at 22° C. with 0.2 nM [$^3$H]4-DAMP in the absence or presence of the test compound in a buffer containing 10 mM Tris-HCl (pH 7.4) and 2 mM EDTA. Non-specific binding is determined in the presence of 1 µM atropine. Following incubation, the samples are filtered rapidly under vacuum through glass fiber filters (GF/B, Packard) presoaked with 0.3% PEI and is rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 4-DAMP, which is tested in each experiment at several concentrations to obtain a competition curve from which its $IC_{50}$ is calculated.

Neuronal Nicotinic Receptor (α-BGTX-insensitive) (Agonist Radioligand):

The purpose is to evaluate the affinity of compounds for the agonist site of the α-BGTX-insensitive central nicotinic receptor in the rat cerebral cortex determined in a radioligand binding assay according to Pabreza et al in Mol. Pharmacol. (1991) 39:9. The experimental protocol is as follows. Membrane homogenates of cerebral cortex (800 µg protein) are incubated for 75 minutes at 4° C. with 1.5 nM [$^3$H]cytisine in the absence or presence of the test compound in a buffer containing 50 mM Tris-HCl (pH 7.4), 120 mM NaCl, 5 mM KCl, 1 mM $MgCl_2$ and 2 mM $CaCl_2$. Non-specific binding is determined in the presence of 10 µM nicotine. Following incubation, the samples are filtered rapidly under vacuum through glass fiber filters (Filtermat B, Wallac) presoaked with 0.3% PEI and rinsed several times with ice-cold 50 mM Tris-HCl using a 48-sample cell harvester (Mach II, Tomtec). The filters are dried then counted for radioactivity in a scintillation counter (Betaplate 1204, Wallac) using a solid scintillator (Meltilex B/HS, Wallac). The results are expressed as a percent inhibition of the control radioligand specific binding. The standard reference compound is nicotine, which is tested in each experiment at several concentrations to obtain a competition curve from which its $IC_{50}$ is calculated.

Neuronal Nicotinic Receptor (α-BGTX-sensitive)

The purpose is to evaluate the affinity of compounds for the α-BGTX-sensitive central nicotinic receptor in the rat cerebral cortex determined in a radioligand binding assay according to Sharples et al in J. Neurosci. (2000) 20:2783. The experimental protocol is as follows. Membrane homogenates of cerebral cortex (400 µg protein) are incubated for 150 minutes at 37° C. with 1 nM [$^{125}$I]α-bungarotoxin in the absence or presence of the test compound in a is buffer containing 50 mM $K_2HPO_4/KH_2PO_4$ (pH 7.4), 10 mM $MgCl_2$ and 0.1% BSA. Non-specific binding is determined in the presence of 1 µM α-bungarotoxin. Following incubation, the samples are filtered rapidly under vacuum through glass fiber filters (Filtermat B, Wallac) presoaked with 0.3% PEI and rinsed several times with an ice-cold buffer containing 50 mM $K_2HPO_4/KH_2PO_4$, 150 mM NaCl and 0.1% BSA using a 48-sample cell harvester (Mach II, Tomtec). The filters are dried then counted for radioactivity in a scintillation counter (Betaplate 1204, Wallac) using a solid scintillator (Meltilex B/HS, Wallac). The results are expressed as a percent inhibition of the control radioligand specific binding. The standard reference compound is α-bungarotoxin, which is tested in each experiment at several concentrations to obtain a competition curve from which its $IC_{50}$ is calculated.

Human Muscle-type Nicotinic Receptor

The purpose is to evaluate the affinity of compounds for the human muscle-type nicotinic receptor expressed in TE671 cells determined in a radioligand binding assay according to Lukas in J. Neurochem. (1986) 46:1936. The experimental protocol is as follows. Cell membrane homogenates (60 µg protein) are incubated for 120 minutes at 22° C. with 2.5 nM [$^{125}$I]α-bungarotoxin in the absence or presence of the test compound in a buffer containing 20 mM Hepes/NaOH (pH 7.3), 118 mM NaCl, 4.8 mM KCl, 2.5 mM $CaCl_2$, 1.2 mM $MgSO_4$ and 0.1% BSA. Non-specific binding is determined in the presence of 5 µM α-bungarotoxin. Following incubation, the samples are filtered rapidly under vacuum through glass fiber filters (GF/B, Packard) presoaked with 0.3% PEI and rinsed several times with an ice-cold buffer containing 50 mM Tris-HCl, 150 mM NaCl and 0.1% BSA using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is a-bungarotoxin, which is tested in each experiment at several concentrations to obtain a competition curve from which its $IC_{50}$ is calculated.

Non-selective Serotonin (5-HT) Receptor (Agonist Radioligand)

The purpose is to evaluate the affinity of compounds for the agonist site of the non-selective 5-HT receptor in the rat cerebral cortex determined in a radioligand binding assay according to Peroutka et al in Mol. Pharmacol. (1979) 16:687. The experimental protocol is as follows. Membrane homogenates of cerebral cortex (144 µg protein) are incubated for 60 minutes at 37° C. with 2 nM [$^3$H]serotonin in the absence or presence of the test compound in a buffer containing 50 mM Tris-HCl (pH 7.4), 4 mM $CaCl_2$, 10 µM pargyline and 1 g/l ascorbic acid. Non-specific binding is determined in the presence of 10 µM serotonin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is serotonin, which is tested in each experiment at several concentrations to obtain a competition curve from which its $IC_{50}$ is calculated.

$Cl^-$ Channel (GABA-gated)

The purpose is to evaluate the affinity of compounds for the $Cl^-$ channel in the rat cerebral cortex determined in a radioligand binding assay according to Lewin et al in Mol. Pharmacol. (1989) 35:189. The experimental protocol is as follows. Membrane homogenates of cerebral cortex (120 µg protein) are incubated for 120 minutes at 22° C. with 3 nM [$^{35}$S]TBPS in the absence or presence of the test compound in a buffer containing 50 mM $Na_2HPO_4/KH_2PO_4$ (pH 7.4) and 500 mM NaCl. Non-specific binding is determined in the presence of 20 µM picrotoxinin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is picrotoxinin, which is tested in each experiment at several concentrations to obtain a competition curve from which its $IC_{50}$ is calculated.

The results of these 18 binding assays, based on an average of two measurements, are reported in table 2 below.

TABLE 2

| | OH | | N |
|---|---|---|---|
| | EPB001 | | EPB002 |

| | % inhibition | |
|---|---|---|
| receptor | EPB001 | EPB002 |
| alpha 1 (non-selective) (antagonist radioligand) | −8 | −3 |
| alpha 2 (non-selective) (antagonist radioligand) | 1 | 8 |
| beta 1 (h) (agonist radioligand) | 3 | 7 |
| beta 2 (h) (agonist radioligand) | 9 | 7 |
| BZD (central) (agonist radioligand) | −10 | −18 |
| CB1 (h) (agonist radioligand) | 13 | −1 |
| D1 (h) (antagonist radioligand) | 13 | 4 |
| D2S (h) (antagonist radioligand) | 1 | 2 |
| GABA (non-selective) (agonist radioligand) | 20 | 8 |
| glycine (strychnine-sensitive) (antagonist radioligand) | −12 | −30 |
| M1 (h) (antagonist radioligand) | 3 | −3 |
| M2 (h) (antagonist radioligand) | 8 | 13 |
| M3 (h) (antagonist radioligand) | −7 | 12 |
| N neuronal alpha-BGTX-insensitive (alpha 4beta 2) (agonist radioligand) | 78 | 66 |
| N neuronal alpha-BGTX-sensitive (alpha 7) (antagonist radioligand) | 8 | 11 |
| N muscle-type (h) (antagonist radioligand) | 16 | 10 |
| 5-HT (non-selective) (agonist radioligand) | 6 | −4 |
| Cl- channel (GABA-gated) (antagonist radioligand) | 0 | 1 |

All publications and patent applications mentioned in this specification are herein incorporated by reference.

Other embodiments are within the following claims.

What is claimed is:

1. A 1-substituted-7-azabicyclo[2.2.1]heptyl derivative represented by the structural formula (I):

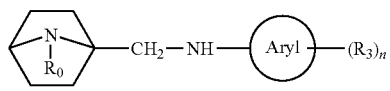

or the structural formula (II):

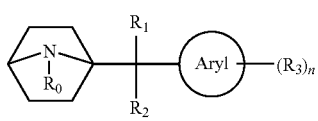

wherein:
$R_0$ is hydrogen or a nitrogen-protecting group selected from the group consisting of benzyl, heteroarylmethyl, heteroarylethyl, phenylethyl, naphthylmethyl, naphthylethyl, butoxycarbonyl, $C_{3-4}$ alkenyl and $C_{1-8}$ alkyl, wherein said benzyl is optionally substituted with one to three substituents is independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl;

$R_1$ is hydrogen and $R_2$ is hydroxyl, or $R_1$ in combination with $R_2$ is oxo or imino;

each $R_3$ is a substituent selected from the group consisting of fluoro, chloro, bromo, $C_{1-4}$ alkyl, $C_{1-4}$ alkoxy, $C_{1-4}$ alkylthio, cyano, phenyl, trifluoromethyl, trifluoromethoxy, amino, dimethylamino, heteroaryl and tert-butylcarboxylate; and n is 0, 1, 2 or 3; and Aryl is an optionally substituted aryl or heteroaryl group, or a pharmaceutically acceptable salt thereof, or a stereochemically isomeric form thereof, or a solvate thereof.

2. A 1-substituted-7-azabicyclo[2.2.1]heptyl derivative according to claim 1, or a pharmaceutically acceptable salt thereof, or a stereochemically isomeric form thereof, or a solvate thereof, wherein Aryl is a non-substituted, mono-substituted, di-substituted or tri-substituted phenyl group.

3. A 1-substituted-7-azabicyclo[2.2.1]heptyl derivative according to claim 1, or a pharmaceutically acceptable salt thereof, or a stereochemically isomeric form thereof, or a solvate thereof, wherein Aryl is an optionally substituted pyrid-3-yl or pyrid-2-yl group.

4. A 1-substituted-7-azabicyclo[2.2.1]heptyl derivative according to claim 3, wherein n is 0 or 1.

5. A 1-substituted-7-azabicyclo[2.2.1]heptyl derivative according to claim 4, wherein $R_3$ is chloro.

6. A 1-substituted-7-azabicyclo[2.2.1]heptyl derivative according to claim 4, being represented by the structural formula (I).

7. A 1-substituted-7-azabicyclo[2.2.1]heptyl derivative according to claim 6, wherein $R_0$ is hydrogen, and n is 0.

8. A 1-substituted-7-azabicyclo[2.2.1]heptyl derivative according to claim 3, being represented by the structural formula (II) wherein $R_1$ is hydrogen and $R_2$ is hydroxyl.

9. A 1-substituted-7-azabicyclo[2.2.1]heptyl derivative according to claim 4, being represented by the structural formula (II) wherein $R_1$ is hydrogen and $R_2$ is hydroxyl.

10. A 1-substituted-7-azabicyclo[2.2.1]heptyl derivative according to claim 9, wherein $R_0$ is hydrogen, and n is 0.

11. A 1-substituted-7-azabicyclo[2.2.1]heptyl derivative according to claim 3, wherein $R_0$ is benzyl substituted in ortho and/or para positions with one to three methoxy groups.

12. A 1-substituted-7-azabicyclo[2.2.1]heptyl derivative according to claim 4, wherein $R_0$ is benzyl substituted in ortho and/or para positions with one to three methoxy groups.

13. A 1-substituted-7-azabicyclo[2.2.1]heptyl derivative according to claim 5, wherein $R_0$ is benzyl substituted in ortho and/or para positions with one to three methoxy groups.

14. A method for producing a 1-substituted-7-azabicyclo[2.2.1]heptyl derivative according to claim 1 and being represented by the structural formula (II) wherein $R_1$ is hydrogen and $R_2$ is hydroxyl, comprising reacting a 1-formyl-7-$R_0$-substituted-7-azabicyclo[2.2.1]-heptane, wherein $R_0$ is as defined in claim 1, with an optionally substituted aryl iodide, aryl chloride or aryl bromide represented by the structural formula Y-Aryl-$(R_3)_n$ wherein Y is iodo, chloro or bromo, and wherein Aryl, n and $R_3$ are as defined in claim 1.

15. A method according to claim 14, wherein $R_0$ is not hydrogen, further comprising the step of cleaving off the nitrogen-protecting group $R_0$.

16. A method for producing a 1-substituted-7-azabicyclo[2.2.1]heptyl derivative according to claim 1 and being represented by the structural formula (II) wherein $R_1$ in combination with $R_2$ is oxo, comprising reacting a 1-cyano-7-$R_0$-substituted-7-azabicyclo[2.2.1]-heptane, wherein $R_0$ is as defined in claim 1, with an optionally substituted aryl iodide, aryl chloride or aryl bromide represented by the structural formula Y-Aryl-$(R_3)_n$ wherein Y is iodo, chloro or bromo, and wherein Aryl, n and $R_3$ are as defined in claim 1.

17. A method according to claim 16, wherein $R_0$ is not hydrogen, further comprising the step of cleaving off the nitrogen-protecting group $R_0$.

18. A method for producing a 1-substituted-7-azabicyclo[2.2.1]heptyl derivative according to claim 1 and being represented by the structural formula (I) comprising submitting a 1-aminomethyl-7-$R_0$-substituted-7-azabicyclo[2.2.1]-heptane, wherein $R_0$ is as defined in claim 1, to a reaction step with an optionally substituted aryl iodide, aryl chloride or aryl bromide represented by the structural formula Y-Aryl-$(R_3)_n$ wherein Y is iodo, chloro or bromo, and wherein Aryl, n and $R_3$ are as defined in claim 1.

19. A method according to claim 18, wherein said reaction is a Buchwald-Hartwig cross-coupling reaction.

20. A method according to claim 18, wherein said reaction is performed in the presence of a palladium complex catalyst.

21. A method according to claim 18, wherein $R_0$ is not hydrogen, further comprising the step of cleaving off the nitrogen-protecting group $R_0$.

22. A pharmaceutical composition comprising a therapeutically effective amount of a 1-substituted-7-azabicyclo[2.2.1]heptyl derivative according to claim 1.

23. A pharmaceutical composition according to claim 22, wherein $R_0$ is hydrogen.

24. A pharmaceutical composition according to claim 22, further comprising one or more pharmaceutically acceptable excipients.

25. A 1-formyl-7-$R_0$-substituted-7-azabicyclo[2.2.1]-heptane or 1-cyano-7-$R_0$-substituted-7-azabicyclo[2.2.1]-heptane, wherein $R_0$ is hydrogen or a nitrogen-protecting group selected from the group consisting of benzyl, phenylethyl, naphthylmethyl, naphthylethyl, butoxycarbonyl, $C_{3-4}$ alkenyl and $C_{1-8}$ alkyl, wherein said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylamino-propoxy, morpholinoethoxy, phenoxy, phenoxymethyl, heteroaryl and heteroarylmethyl.

26. A method for producing a 1-cyano-7-$R_0$-substituted-7-azabicyclo[2.2.1]-heptane comprising reacting 4-methanesulfonyl-cyclohexanone with a molar excess of a primary amine $R_0NH_2$, wherein $R_0$ is selected from the group consisting of benzyl, phenylethyl, naphthylmethyl, naphthylethyl, butoxy-carbonyl, $C_{3-4}$ alkenyl and $C_{1-8}$ alkyl, wherein said benzyl is optionally substituted with 1 to 3 substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl.

27. A method for producing a 1-cyano-7-$R_0$-substituted-7-azabicyclo[2.2.1]-heptane according to claim 26, wherein $R_0$ is benzyl substituted in ortho position and/or para position with one to three methoxy groups.

* * * * *